United States Patent [19]
Frei et al.

[11] Patent Number: 5,610,195
[45] Date of Patent: Mar. 11, 1997

[54] ORNITHINE DECARBOXYLASE INHIBITING BRANCHED AMINOOXY AMINO ALKANE DERIVATIVES

[75] Inventors: Jörg Frei, Hölstein; Jaroslav Stanek, Arlesheim, both of Switzerland

[73] Assignee: Ciba-Geigy Corporation, Tarrytown, N.Y.

[21] Appl. No.: 351,336

[22] PCT Filed: Apr. 2, 1994

[86] PCT No.: PCT/EP94/01036

§ 371 Date: Dec. 12, 1994

§ 102(e) Date: Dec. 12, 1994

[87] PCT Pub. No.: WO94/24094

PCT Pub. Date: Oct. 27, 1994

[30]    Foreign Application Priority Data

Apr. 13, 1993 [CH]  Switzerland ............... 1129/93

[51] Int. Cl.$^6$ ........................................ A61K 31/13
[52] U.S. Cl. ........................... 514/645; 564/301
[58] Field of Search .................. 564/301; 514/645

[56]    References Cited

U.S. PATENT DOCUMENTS

| 3,137,705 | 6/1964 | Prelog et al. | 260/326 |
|---|---|---|---|
| 3,869,278 | 3/1975 | Wilcox | 71/121 |
| 4,425,340 | 1/1984 | Teraji et al. | 424/246 |

FOREIGN PATENT DOCUMENTS

| 0291957 | 11/1988 | European Pat. Off. |
|---|---|---|
| 0321274 | 6/1989 | European Pat. Off. |
| 0395174 | 10/1990 | European Pat. Off. |
| 0412763 | 2/1991 | European Pat. Off. |
| 0483427 | 6/1992 | European Pat. Off. |
| 3501616 | 7/1986 | Germany. |
| 0974163 | 11/1964 | United Kingdom. |

OTHER PUBLICATIONS

Khomutov R. et al "Aminooxypropylamine as an Effective Inhibitor of Ornithine Decarboxylase In vitro and In vivo" Chem. Abs. 104: 30840g (1986).
Moyano et al "Inhibition of Ornithine Decarboxylase by the Isomers of 14–Dimethylputrescine" J Med Chem. vol. 33 (1969).
Ruiz et al "Effect of N–Alkyl and C–Alkylputrescines on the Activity of ornithine Decarboxylase from Rat Liver and *E coli*" Biochem. Biophys Acta 873 (1986).
Stanek et al "2–Substituted 3–(Aminoxy) Propanamines as Inhibitors of Ornithine Decarboxylase: Synthesis and Biological Activity" J Med Chem vol. 35 (1992) 1339–1344.
Smith et al "Growth Inhibition of Botrytis Cinerea by Compounds Interfering with Polyamine Metabolism" Journal of General Microbiology, vol. 136 (1990) 985–992.
Poulin et al "Effect of 1–Amino–Oxy–3–Aminopropane on Polyamine Metabolism and Growth of L1210 Cells" J. of Biochem vol. 263 (1989) 215–221.

Khomutov et al "An Aminooxy Analog of Putrescine Inhibits the Polyketide Pathway of the Biosynthesis of Natural Compounds" Sowjet J of Bioorganic Chem. vol. 394 (1990).
Mett et al "Pharmacological Properties of the Ornithine Decarboxylase Inhibitor 3–Aminooxy–1–Propanamine and Several Structural Analogues" Cancer Chemother. Phar. vol. 32 (1993).
Keinanen et al "Application of Oxime Formation in a Radiometric Assay of Aminooxy Compounds" Analytical Biochem 208, (1993) 35–43.
Pankaskie et al "An Improved Synthetic Route to Aminoxypropylamine (APA), and Related Homologs" Synthetic Comm. 19. (3 & 4) 1989 pp. 339–344.
Hyvonen et al "1–aminooxy–3–Aminopropane Reversibly Prevents the Proliferation of Cultured Baby Hamster Kidney Cells by Interfering with Polyamine Synthesis" J. Biol Chem. vol. 263 (23) 1988 pp. 11138–1144.
Christ et al "Inhibitors Influencing Plant Enzymes of the Polyamine Biosynthetic Pathway" Z. Naturforschg. C. Biosci 44 (1989) 49–54.
Felix et al "Influence of Inhibitors of Polyamine Biosynthesis on Polyamine Levels and Growth of Plants" Z. Naturforschg. C. Biosci. 44, (1989) 55–58.
Hyvonen et al "Monitoring of the Uptake and Metabolism of Aminooxy Analogues of Polyamines in Cultured Cells by High–Performance Liquid Chromatography" Journal of Chromatography. 574 (1992) pp. 17–21.
Paulin et al "Ornithine Decarboxylase, S–Adenosyl–L–Methionine Decarboxylase and Arginine Decarboxylase from. Mycobacterinmbovis (BCG)" Experientia 43. (1987) pp. 174–176.
Hyvonen et al "Uptake of $^3$H–Labeled 1–Aminooxy–3–Aminopropane by Baby Hamster Kidney Cells" J. Biochem. 107 (1990) pp. 817–820.
Hyvonen et al "Regulation of S–Adenosyl–L–Methionine Decarboxylase by 1–Aminooxy–3–Aminopropane: Enzyme Kinetics and Effects on the Enzyme Activity in Cultured Cells" J. Biochem 107 (1990) pp. 339–342.

(List continued on next page.)

Primary Examiner—Brian M. Burn
Attorney, Agent, or Firm—Gregory D. Ferraro; Karen G. Kaiser

[57]    ABSTRACT

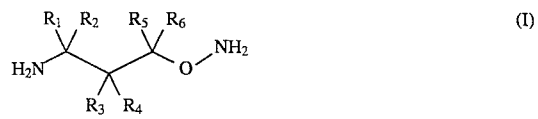

Compounds of formula (I) in which (a) four of the radicals $R_1$, $R_2$, $R_3$, $R_4$, $R_5$ and $R_6$ are hydrogen and the others independently of one another are in each case $C_1$–$C_2$alkyl, these groups being bonded to the same carbon atom or to two different carbon atoms, or (b) five of the radicals $R_1$, $R_2$, $R_3$, $R_4$, $R_5$ and $R_6$ are hydrogen and the other radical is $C_1$–$C_2$alkyl or hydroxymethyl, or salts thereof, are described. The compounds of formula (I) and their salts are ornithine decarboxylase inhibitors.

39 Claims, No Drawings

OTHER PUBLICATIONS

Paulin "The Effects of 1–Aminooxy–3–Aminopropane and S–(5–Deoxy–5–Adenosyl) Methylthioethylhydroxylamine on Ornithine Decarboxylase and S–Adenosyl–L–Methionine Decarboxylase from *Escherichia coli*" FEBS Lett vol. 202 (2) 1986 pp. 323–326.

Khomutov et al "Polyfunctional O–Substituted Hydroxylamines for Specific Inhibition of Enzymes and Modification of Nucleic Acids" F.E.C.S Int. Conf. Chem Biotechnol., Biol. Act. Nat Prod. (Proceedings) 3rd Meeting Date (1985) vol. 1, 214–8 (1987).

Pankaskie et al "The Preparation of 3–Aminoxy–1–Amino [1, $1^1$–$^3H_2$] propane" J of Label Comp. Radiopharm. XXVII (2) 167–70 (1989);.

Khomutov et al "Chemical Regulation of Polyamine Biosynthesis in Cell Cultures by Polyfunctional O–Substituted Hydroxylamines" Fukui, T. (Ed.) Enzymes. Depend. Pyridoxal Phosphate Other Carbonyl Compound Cofactors, Proc. Lat. Symp. Vitamin B 6, 56 7–9, Pergamon, Oxford 1991.

Khomutov et al "Synthesis of Aminooxy, Analogs of Putrescine and Spermidine" Bioorg. Khim 15 (5) 698–707 (1989) Corresponds to Sowjet J. Bioorganic Chem. 386–91 (1990).

Khomutov et al "New Inhibitors of Caronsine Synthetase Based on Analogs of B–Alanyl Adenylate and B–Alanyl Phosphate" Bioorg. Khim 15(5) 627–33 (1989) Corresponds to Sowjet J. Bioorganic Chem. 33–8 (1990).

Casara et al "Stereospecific Synthesis of (2R, 5R)—Hept–6–Yne–2, 5–Diamine: A Potent and Selective Enzyme–Activated Irreversible Inhibitor of Ornithine Decarboxylase (ODC)" J. Chem. Soc. Perkin Trans. 1 (1985) 2201–7.

92–286002/35 Derwent Abstract Corresponds to EPO–499–823 (1992).

90–284488/38 Derwent Abstract Corresponds to EP 388–309–A. (1990).

93–176983/22 Derwent Abstract Corresponds to EP 0 544 168. (1993).

Singh et al "Antimalarials 7–Chloro–4–(Substituted Amino) Quinolines" J. Med. Chem. 14(4) 283–6 (1971).

76970X/41 Derwent corresponds to NL 750 33 13. (1975).

Eloranta et al "Aminooxy Analogues of Polyamines as New Tools in Unraveling the Physiology of Putrescine Spermidine and Spermine" Life Chemistry Reports 9, 163–9 (1991).

90–158011/21 Derwent Corresponds to AU 44711/89 (Text is Enclosed as English Equivelant. (1990).

Derivatives of 1–Aminooxy–3–Aminopropane as Polyamine Antimetabolites J. Biochem. 116(5) 1056–62 (1994, Nov.).

ORNITHINE DECARBOXYLASE INHIBITING BRANCHED AMINOOXY AMINO ALKANE DERIVATIVES

This application is a 371 of PCT/EP94/01036, filed Apr. 4, 1994.

The present invention relates to novel pharmaceutically active aminooxy compounds, processes for the preparation of these compounds, pharmaceutical compositions comprising these compounds, these compounds for use in a prophylactic, therapeutic or diagnostic method for the treatment of the human or animal body, and the use of these compounds for the prophylactic or therapeutic treatment of the human or animal body and for the preparation of pharmaceutical compositions.

According to the current state of knowledge, there are a number of states of the human or animal body which can be influenced favourably by inhibition of polyamine biosynthesis.

The enzyme ornithine decarboxylase (ODC) is one of the key enzymes of polyamine biosynthesis. A reduction in the activity of ODC leads to a reduced polyamine biosynthesis and therefore to reduced polyamine levels in the cell. If inhibition of the activity of this enzyme by ODC inhibitors can be achieved, the polyamine concentration in mammalian cells (including human cells) can be influenced, i.e. lowered, with the aid of such ODC inhibitors.

In mammalian cells, ODC catalyses the synthesis of putrescine, an intermediate in polyamine biosynthesis. The breakdown of putrescine in the cell is effected in particular by diamine oxidase (DAO). If the DAO is active, excess putrescine can be broken down, which further promotes the action of an ODC inhibitor. The less an inhibitor of ODC inhibits DAO, i.e. the higher its specificity, the more advantageous its properties.

The compound of the formula

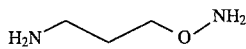

with the name 1-aminooxy-3-aminopropane (APA) is known. This compound is a potent inhibitor of ODC, but is not selective with respect to diamine oxidase. Furthermore, according to Eloranta et at., Life Chemistry Reports Volume 9, 163–169 (1991), it has practically no action in whole animal tests.

It has now been found, surprisingly, that the compounds according to the invention described in this invention which carry, on the central carbon chain, substituents which are bonded directly to the central carbon chain merely by a non-polar carbon atom belonging to the substituent, and the terminal polar groups of which are partly sterically hindered and protected from metabolic breakdown by the substituents mentioned, have advantageous pharmacological properties.

The compounds are potent inhibitors of ornithine decarboxylase.

Compared with APA, the compounds of the present invention tested show, for example, an increased selectivity in the inhibition of ODC with respect to inhibition of DAO.

The compounds of the formula I investigated furthermore are active in vivo and are also tolerated well at high doses.

The compounds according to the invention are those of the formula I

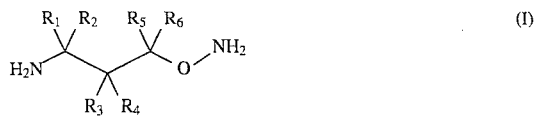

in which a) four of the radicals $R_1$, $R_2$, $R_3$, $R_4$, $R_5$ and $R_6$ are hydrogen and the others independently of one another am in each case $C_1$–$C_2$alkyl, these groups being bonded to the same carbon atom or to two different carbon atoms, or b) five of the radicals $R_1$, $R_2$, $R_3$, $R_4$, $R_5$ and $R_6$ are hydrogen and the other radical is $C_1$–$C_2$alkyl or hydroxymethyl, or salts thereof.

The compounds of the present invention can in some cases exist as pure enantiomers or enantiomer mixtures, for example racemates. A condition for this is that only one or two of the substituents $R_1$, $R_2$, $R_3$, $R_4$, $R_5$ and $R_6$ (bonded to two different carbon atoms) is or are as defined, except for hydrogen (i.e. one of these radicals is $C_1$–$C_2$alkyl or hydroxymethyl, or two of these radicals, which are bonded to two different carbon atoms, are $C_1$–$C_2$alkyl), while the others are hydrogen; or that, if two of these radicals are $C_1$–$C_2$alkyl and are bonded to one carbon atom, these two radicals are not identical. If the two $C_1$–$C_2$alkyl radicals are bonded to two different carbon atoms, the compounds of the formula I can also exist as diastereomer mixtures (with or without optical activity). In all these cases, compounds of the formula I having one or two asymmetric carbon atoms which can exist in the (R), the (S) or the (R,S) configuration, preferably in the (R) or (S) configuration, i.e. as pure enantiomers, exist.

The terms and general expressions used in the description of the present invention preferably have the following meanings:

$C_1$–$C_2$Alkyl is methyl or ethyl.

If four of the radicals $R_1$, $R_2$, $R_3$, $R_4$, $R_5$ and $R_6$ are hydrogen and the others independently of one another are in each case $C_1$–$C_2$alkyl, these alkyl groups are preferably bonded to the same carbon atom.

Salts of compounds according to the invention are acid addition salts, in particular pharmaceutically acceptable acid addition salts, i.e. those acid addition salts which do not have a noticeable toxicity in the particular doses to be used, for example salts with inorganic acids, such as hydrochloric acid, sulfuric acid or phosphoric acid, or with suitable organic carboxylic or sulfonic acids, for example acetic acid, octanoic acid, succinic acid, adipic acid, fumaric acid, maleic acid, hydroxymaleic acid, propionic acid, lactic acid, malic acid, citric acid, salicylic acid, p-aminosalicylic acid, ascorbic acid, oxalic acid, benzenesulfonic acid, 1,5-naphthalenedisulfonic acid, methanesulfonic acid or 1,2-ethanedisulfonic acid, with N-cyclohexylsulfamic acid or, for example, with amino acids, such as glutamic acid or aspartic acid. Mono- or disalts can be formed, depending on the basicity of the basic groups present.

Pharmaceutically unsuitable salts, for example picrates or perchlorates, can also be used for isolation or purification. Only the pharmaceutically acceptable salts are used therapeutically and are therefore preferred.

The compounds according to the invention have useful, in particular pharmacologically usable, properties. Surprisingly, it has been found that the compounds of the formula I in particular have a potent, specific inhibiting action on the enzyme ornithine decarboxylase (ODC), which is selective with respect to diamine oxidase (DAO). They are a novel class of ODC inhibitors.

ODC plays an important role as a key enzyme in polyamine biosynthesis, which proceeds in practically all cells of mammals, including humans. The polyamine concentration in the cell is regulated by ODC. Inhibition of the enzyme ODC results in a reduction in the polyamine concentration. Since a reduction in the polyamine concentration causes an inhibition of cell growth, it is possible by administering ODC-inhibiting substances to inhibit the growth of eukaryotic and also of prokaryotic cells, in particular of rapidly or uncontrollably growing cells, and even to kill cells or to inhibit the onset of cell differentiation.

The inhibition of the enzyme ODC can be demonstrated, for example, by the method of J. E. Seely and A. E. Pegg, Ornithine Decarboxylase (Mouse Kidney), pages 158–161, in H. Tabor and C. White-Tabor (editors): Methods in Enzymology, Volume 94: Polyamines, Academic Press, New York 1983. If ODC from the rat liver is used in this test (isolation: Hayashi, S. I. and Kameji, T., same volume, pages 154–158), $IC_{50}$ values in the micromolar range down to about 0.01 µM, preferably between about 0.01 and 1 µM, for example between 0.014 and 0.7 µM, are obtained for compounds of the formula I. $IC_{50}$ is the concentration of the inhibitor at which the ODC activity is 50% of a control without inhibitor.

The selectivity of the inhibition of ODC with respect to diamine oxidase (DAO) is demonstrated by the following test system (cf. Seppänen et al., in: Polyamines, Tabor, H., and White-Tabor, C. (editors), Methods Enzymol. 94, 274–253, Academic Press, New York & London 1983): DAO from pig kidney (obtainable from Sigma Chemie, Deisenhofen, Germany) is employed in particular as the enzyme instead of the enzyme from the rat small intestine. Briefly, the batch contains (expressed as the final concentrations) 0.1M potassium phosphate buffer pH 7.4; 10 mM mercaptoethanol, 0.40 mM putrescine, including 40 nCi [1,4-$^{14}$C]putrescine (Amersham, 110 Ci/mole) and variable amounts of enzyme protein (DAO) and inhibitor. For standard experiments, the batches are incubated for 30 minutes at 37° C. and then transferred to an ice-bath. The reaction is stopped by addition of 0.5 ml of ice-cold 1M $Na_2CO_3$ solution which contains 1 mM aminoguanidine. After addition of 4 ml of toluene with 5 g/l of PPO (2,5-diphenyloxazole), the test tube is continuously inverted around the transverse axis at room temperature for 10 minutes, for mixing, and is then centrifuged at 1800×g in a centrifugal rotor at 4° C. for 5 minutes and finally frozen in ethanol/dry ice. The liquid upper phase is transferred to a scintillation glass, the frozen lower phase is thawed by incubation for 5 minutes at 37° C., 4 ml of toluene/PPO are added again and the mixture is extracted again as above. After a total of 3 extractions, the combined toluene extracts (which contain the radiolabelled 1-pyrroline to the extent that it has been liberated from putrescine by the action of the DAO) are measured in a liquid scintillation counter (Rack Beta 1215, LKB-Wallac). For calculation of the radioactivity employed, an aliquot of the aqueous phase after 3 extractions is transferred to Whatman GF/C filter (glass fibre filter, Whatman, USA), dried in vacuo and, after addition of 5 ml of toluene/PPO, is counted. For determination of the extraction blank values, a control which contains 25 mM Tris/1 mm EDTA/1 mM dithiothreitol pH 7.4 instead of DAO is used in each test series. The inhibitor concentrations at which 50% inhibition exists compared with the non-inhibited DAO are determined from the linear regression of the log(inhibitor concentration) against the relative DAO activity (% of the non-inhibited control), only relative activities of between 95 and 5% being included in the calculation.

The numerical ratio of the $IC_{50}$ for the DAO inhibition to the $IC_{50}$ for the ODC inhibition [quotient of $IC_{50}$(DAO)/$IC_{50}$(ODC)] is preferably more than 150 to about 800 for the compounds according to the invention, which demonstrates a high selectivity of inhibition of ODC with respect to DAO; in contrast, the corresponding quotient for APA is about 1.2

As ODC inhibitors, the compounds of the formula I have antiproliferative properties, which can be demonstrated, for example, by demonstration of the inhibiting action on the growth of human T24 bladder carcinoma cells. The demonstration is effected by a procedure in which these cells are incubated in "Eagle's minimal essential medium", to which 5% (V/V) of foetal calf serum is added, in air in a humidified incubator at 37° C. and 5 per cent by volume of $CO_2$. The carcinoma cells (1000–1500) are transinoculated into 96-well microtitre plates and incubated overnight under the conditions mentioned. The test substance is added in serial dilutions on day 1. The plates are incubated under the conditions mentioned for 5 days. During this period of time, the control cultures pass through at least 4 cell divisions. After the incubation, the cells are fixed with 3.3% (weight/volume=w/v) aqueous glutaraldehyde solution, washed with water and stained with 0.05% (w/v) aqueous methylene blue solution. After washing, the dye is eluted with 3% (w/v) aqueous hydrochloric acid. Thereafter, the optical density (OD) per depression, which is directly proportional to the number of cells, is measured with a photometer (Titertek multiskan) at 665 nm. The $IC_{50}$ values are calculated with a computer system using the formula $$IC_{50} = \frac{OD_{665} \text{ (test)} - OD_{665} \text{ (initial)}}{OD_{665} \text{ (control)} - OD_{665} \text{ (initial)}} \times 100$$

The $IC_{50}$ values are defined as that concentration of active ingredient at which the number of cells per depression at the end of the incubation time is only 50% of the number of cells in the control cultures. The $IC_{50}$ values of the compounds of the formula I are preferably in the range from $10^{-6}$ to $1.5 \times 10^{-4}$ M.

The compounds of the formula I are thus particularly suitable for the treatment of disease states which respond to inhibition of ornithine decarboxylase, for example benign and malignant tumours. They can cause turnout regressions, and furthermore prevent the spread of tumour cells and the growth of micrometastases. They moreover can be used, for example, for the treatment of protozoa infections, such as, for example, trypanosomiasis, malaria or inflammation of the lung caused by Pneumocystis carinii.

Compounds of the formula I can be tolerated well here. This can be demonstrated by tests on rats: healthy male albino rats (Tif:RAIf (SPF), CIBA Animal Production, Stein, Switzerland) of initially 130 to 250 g are supplied with a pelleted standard diet (NAFAG No. 890; NAFAG, Gossau, Switzerland) and water ad libitum. 20, 60 or 200 mg/kg of a compound of the formula I in 10 ml of aqueous solution (concentrations 0.2; 0.6; and 2.0%) are additionally administered daily to the rats for 14 days by separate artificial feeding. The following data, for example, are determined during the administration period: mortality, clinical symptoms, body weight, food consumption, water consumption, hearing, clinical biochemistry, haematology, urine analysis, necropsy). Result: compounds of the formula I investigated are tolerated without obvious signs of toxicity at doses of up to 200 mg/kg daily.

As selective ODC inhibitors, the compounds of the formula I can be used by themselves or also in combination with other pharmacologically active substances. Conceivable combinations are, for example, those with (a) inhibitors of other enzymes of polyamine biosynthesis, for example S-adenosylmethionine decarboxylase inhibitors, (b) inhibitors of protein kinase C, (c) inhibitors of tyrosine protein kinase, (d) cytokines, (e) negative growth regulators, (f) aromatase inhibitors, (g) antioestrogens or (h) conventional cytostatic active ingredients.

Preferred compounds of the formula I according to the invention are those in which a) four of the radicals $R_1$, $R_2$, $R_3$, $R_4$, $R_5$ and $R_6$ are hydrogen and the others independently of one another are in each case $C_1$–$C_2$alkyl, in particular methyl, these groups being bonded to different carbon atoms or (preferably) to the same carbon atom, or b) five of the radicals $R_1$, $R_2$, $R_3$, $R_4$, $R_5$ and $R_6$ are hydrogen and the other radical is $C_1$–$C_2$alkyl, in particular methyl;

these compounds, if they contain an asymmetric carbon atom, existing as enantiomer mixtures or pure enantiomers, preferably as pure enantiomers, or salts thereof.

Particularly preferred compounds of the formula I are those in which one of the radicals $R_1$ and $R_2$ is $C_1$–$C_2$alkyl, in particular methyl, and the other is hydrogen and each of the radicals $R_3$, $R_4$, $R_5$ and $R_6$ is hydrogen;

which exist as enantiomer mixtures or as pure enantiomers, and salts thereof.

Particularly preferred compounds of the formula I are also those in which one of the radicals $R_3$ and $R_4$ is $C_1$–$C_2$alkyl, in particular methyl, and the other is hydrogen and each of the radicals $R_1$, $R_2$, $R_5$ and $R_6$ is hydrogen;

which exist as enantiomer mixtures or as pure enantiomers, and salts thereof.

Particularly preferred compounds of the formula I are also those in which one of the radicals $R_5$ and $R_6$ is $C_1$–$C_2$alkyl, in particular methyl, and the other is hydrogen and each of the radicals $R_1$, $R_2$, $R_3$ and $R_4$ is hydrogen;

which exist as enantiomer mixtures or as pure enantiomers, and salts thereof.

Especially preferred compounds of the formula I are those in which one of the radicals $R_1$ and $R_2$ is $C_1$–$C_2$alkyl, in particular methyl, and the other is hydrogen and each of the radicals $R_3$, $R_4$, $R_5$ and $R_6$ is hydrogen;

which exist as pure enantiomers, and salts thereof.

Preferred compounds of the formula I are also those in which one of the radicals $R_1$, $R_2$, $R_3$, $R_4$, $R_5$ and $R_6$ is hydroxymethyl, while each of the other radicals is hydrogen;

the corresponding compounds of the formula I existing as enantiomer mixtures or as pure enantiomers, in particular as pure enantiomers, and salts thereof.

Preferred compounds of the formula I are also those in which each of the radicals $R_1$ and $R_2$ is chosen from hydrogen, $C_1$–$C_2$alkyl (in particular methyl) and hydroxymethyl, in particular from hydrogen and $C_1$–$C_2$alkyl, such as methyl, with the provisos that if one of these two radicals is hydroxymethyl the other is hydrogen, and that not more than one of the two radicals is hydrogen;

and in which $R_3$, $R_4$, $R_5$ and $R_6$ are hydrogen;

these compounds, if the radicals $R_1$ and $R_2$ differ from one another, existing as enantiomer mixtures or as pure enantiomers, preferably as pure enantiomers, in particular as pure (S) enantiomers, and salts thereof.

Particularly preferred compounds of the formula I are those in which one of the radicals $R_1$, $R_2$, $R_3$, $R_4$, $R_5$ and $R_6$ is $C_1$–$C_2$alkyl, in particular methyl;

these compounds existing as enantiomer mixtures or as pure enantiomers, preferably as pure enantiomers; and salts thereof.

Especially preferred compounds of the formula I are those in which one of the radicals $R_1$, $R_2$, $R_3$, $R_4$, $R_5$ and $R_6$ is $C_1$–$C_2$alkyl, in particular methyl;

these compounds existing in the (S) configuration, and salts thereof.

Especially preferred compounds of the formula I are also those in which one of the radicals $R_1$, $R_2$, $R_3$, $R_4$, $R_5$ and $R_6$ is $C_1$–$C_2$alkyl, in particular methyl:

these compounds existing in the (R) configuration, and salts thereof.

The invention relates above all else to the specific compounds of the formula I mentioned in the examples and salts, in particular pharmaceutically acceptable salts, thereof.

The novel compounds of the formula I and their salts can be prepared by processes known per se, for example a procedure in which from a compound of the formula II

$$X_1X_2N-(CR_1R_2)-(CR_3R_4)-(CR_5R_6)-O-NX_3X_4 \quad (II)$$

in which the radicals $R_1$, $R_2$, $R_3$, $R_4$, $R_5$ and $R_6$ are as defined for compounds of the formula I and in which $X_1$, $X_2$, $X_3$ and $X_4$ independently of one another are hydrogen or a monovalent amino-protecting group, and in which X1 with $X_2$, $X_3$ with $X_4$ or $X_1$ with $X_2$ and $X_3$ with $X_4$ can also in each case together be a bivalent protecting group, and in which other functional groups which are not to participate in the reaction are present in protected form if necessary, with the proviso that at least one of the groups $X_1$, $X_2$, $X_3$ and $X_4$ is an amino-protecting group, or from a salt thereof if salt-forming groups are present, amino-protecting groups present are split off, and, if desired, a compound of the formula I which is obtainable is converted into another compound of the formula I, an isomer mixture which is obtainable is split into the isomers and/or a free compound of the formula I which is obtainable is converted into a salt or a salt of a compound of the formula I which is obtainable is converted into the free compound or into another salt.

DETAILED DESCRIPTION OF THE PREFERRED PROCESS VARIANTS

Unless stated otherwise, the radicals $R_1$, $R_2$, $R_3$, $R_4$, $R_5$ and $R_6$ in the starting materials and end products below are as defined for compounds of the formula I.

Elimination of Protecting Groups

The protecting groups for functional groups in starting materials, in particular for amino and hydroxyl groups, include, in particular, the conventional protecting groups which are usually used, for example, in the synthesis of peptide compounds, cephalosporins, penicillins, nucleic acid derivatives and sugars. These protecting groups can already be present in the intermediates and should protect the functional groups in question against undesirable side reactions. It is characteristic of protecting groups that they can be introduced and split off easily, i.e. without undesirable side reactions, and that they are not present in the end products.

Protecting groups and their removal are known per se and are described, for example, in J. F. W. McOmie, "Protective Groups in Organic Chemistry", Plenum Press, London, N.Y., 1973, and T. W. Greene, "Protective Groups in Organic Synthesis", Wiley, N.Y., 1984.

Preferred monovalent amino-protecting groups $X_1$, $X_2$, $X_3$ and $X_4$ are acyl groups, preferably lower alkanoyl, such as formyl, acetyl or propionyl, halo-lower alkanoyl, such as 2-halogenoacetyl, in particular 2-chloro-, 2-bromo-, 2-iodo-, 2,2,2-trifluoro- or 2,2,2-trichloroacetyl, benzoyl which is unsubstituted or substituted, for example by halogen, lower alkoxy, lower alkoxycarbonyl or nitro, for example benzoyl, 4-chlorobenzoyl, 4-methoxybenzoyl, 2-methoxycarbonyl-benzoyl or 4-nitrobenzoyl, the acyl radical of a carbonic acid half-ester, in particular arylmethoxycarbonyl having one or two aryl radicals, which are preferably phenyl, naphthyl or 9-fluorenyl which is unsubstituted or mono- or polysubstituted, for example by lower alkyl, in particular ten-lower alkyl, such as tert-butyl, lower alkoxy, such as methoxy, hydroxyl, halogen, for example chlorine, and/or nitro, such as unsubstituted or substituted benzyloxycarbonyl, for example 4-nitrobenzyloxycarbonyl, or substituted diphenyl-methoxycarbonyl, for example di-(4-methoxy-phenyl)-methoxycarbonyl, 2-halo-lower alkoxycarbonyl, for example 2,2,2-trichloroethoxycarbonyl, 2-bromomethoxy-carbonyl or 2-iodoethoxycarbonyl, lower alkoxycarbonyl, in particular a lower alkoxycarbonyl which is branched in the 1-position of the lower alkyl radical or suitably substituted in the 1- or 2-position, in particular tert-lower alkoxycarbonyl, for example tert-butoxycarbonyl, or primary lower alkoxycarbonyl, such as ethoxycarbonyl, alkylformimidoyl, such as lower alkyl-formimidoyl, for example tert-butyl-formimidoyl, sulfo (—$SO_3H$), which can also exist in salt form, such as in the form of an alkali metal or ammonium salt, for example as the sodium or potassium salt, or aryl-methyl groups, such as mono-, di- or, in particular, triaryl-methyl, the aryl radicals being, in particular, unsubstituted or substituted phenyl radicals, for example benzyl, diphenyl-methyl or triphenylmethyl (trityl). Phenyl-lower alkyl-methyl, such as (R,S)-, (R)- or, in particular, 1 (S)-phenylethyl, is also preferred. Tri-lower alkylsilyl, such as trimethylsilyl, is furthermore possible.

Particularly preferred monovalent amino-protecting groups $X_1$, $X_2$, $X_3$ and $X_4$ are acyl radicals of carbonic acid half-esters, in particular lower alkoxycarbonyl, for example tert-butoxycarbonyl or ethoxycarbonyl, benzyloxycarbonyl which is unsubstituted or substituted, for example as defined above, for example 4-nitro-benzyloxycarbonyl, diphenyl-methoxycarbonyl or 2-halo-lower alkoxycarbonyl, such as 2,2,2-trichloroethoxycarbonyl; trityl; lower alkanoyl, such as formyl and acetyl, 2-methoxy-carbonyl-benzoyl or lower alkylformimidoyl radicals, in particular those in which the lower alkyl radical is branched once or twice in the 1-position, such as tert-butyl-formimidoyl. The protecting group $X_1$ or $X_2$ preferred above all others is lower alkoxycarbonyl, for example tert-butoxycarbonyl, or lower alkanoyl, such as acetyl.

Preferred bivalent amino-protecting groups formed from the radicals $X_1$ and $X_2$ and/or $X_3$ and/or $X_4$ are mono- or disubstituted methylidene groups (resulting in oxime derivatives in the case of $X_3$ and $X_4$), such as 1-lower alkoxy(in particular methoxy or ethoxy)-lower alkylidene (for example -ethylidene or -1-n-butylidene), for example =$C(CH_3)(OC_2H_5)$, 1-lower alkyl(in particular methyl or ethyl)-lower alkylidene (in particular -1-ethylidene), for example =$C(CH_3)_2$, or 1-phenyl-lower alkylidene, for example =CH-phenyl, and hydrocarbyldicarboxylic acid radicals which are preferably bonded via both carbonyl groups to the nitrogen to be protected (resulting in bisacyl derivatives), in particular phthaloyl or hydrogenated analogues which are unsubstituted or substituted, for example by the same substituents as defined above for substituted benzoyl, for example the phthaloyl radical, which forms a 1H-isoindole-1,3(2H)dione radical (phthalimido group) together with the nitrogen atom to be protected, or corresponding dihydro-, tetrahydro- or hexahydro-phthaloyl radicals, lower alkyl-dicarboxylic acid radicals, such as the succinic acid radical, lower alkenyldicarboxylic acid radicals, such as the maleic acid radical, or $C_6$–$C_{12}$bicyclodicarboxylic acid radicals, such as the 5-nor-bornene-2,3-dicarboxylic acid radical.

Other functional groups which can be present in protected form are, in particular, hydroxyl groups which can be present in one of the radicals $R_1$, $R_2$, $R_3$, $R_4$, $R_5$ or $R_6$; the corresponding protecting groups can likewise be mono- or bivalent (in the latter case, hydroxyl and amino can also be protected together, i.e. one or two of the amino-protecting groups $X_1$, $X_2$, $X_3$ and $X_4$ can protect a hydroxyl group with their second bond).

A hydroxyl group can be protected, for example, by a monovalent protecting group, such as an acyl group, for example lower alkanoyl which is unsubstituted or substituted by halogen, such as chlorine, such as acetyl or 2,2-dichloroacetyl, or in particular by an acyl radical of a carbonic acid half-ester mentioned for protected amino groups. A preferred hydroxyl-protecting group is, for example, 2,2,2-trichloroethoxycarbonyl, 4-nitrobenzyloxy-carbonyl or diphenylmethoxycarbonyl. A hydroxyl group furthermore can be protected by tri-lower alkylsilyl, for example trimethylsilyl, triisopropylsilyl, tert-butyl-dimethylsilyl or, in particular, dimethyl-(2,3-dimethyl-2-butyl)silyl (=thexyldimethylsilyl), an etherifying group which can easily be split off, for example an alkyl group, such as ten-lower alkyl, for example tert-butyl, an oxa or a thiaaliphatic or -cycloaliphatic, in particular 2-oxa- or 2-thiaaliphatic or-cycloaliphatic, hydrocarbon radical for example 1-lower alkoxy-lower alkyl or 1-lower alkylthio-lower alkyl, such as methoxymethyl, 1-methoxyethyl, 1-ethoxyethyl, methylthi-omethyl, 1-methylthioethyl or 1-ethylthioethyl, or 2-oxa- or 2-thiacycloalkyl having 5–7 ring atoms, such as 2-tetrahydrofuryl or 2-tetrahydropyranyl, or a corresponding thia analogue, and by 1-phenyl-lower alkyl, such as benzyl, diphenylmethyl or trityl, in which the phenyl radicals can be unsubstituted or substituted, for example by halogen, for example chlorine, lower alkoxy, for example methoxy, and/or nitro.

Two hydroxyl groups present in one molecule, in particular adjacent hydroxyl groups, or an adjacent hydroxyl and amino group can be protected, for example, by bivalent protecting groups, such as a methylene group which is unsubstituted or, preferably, substituted, for example by one or two lower alkyl radicals or oxo, for example by unsubstituted or substituted alkylidene, for example lower alkylidene, such as isopropylidene, cycloalkylidene, such as cyclohexylidene, a carbonyl group or benzylidene.

A protected hydroxyl group is preferably protected by lower alkoxycarbonyl or tri-lower alkylsilyl, in particular by trimethylsilyl, tert-butyl-dimethylsilyl, dimethyl-(2,3-dimethyl-2-butyl)silyl or tert-butoxycarbonyl.

The protecting groups are split off in the process according to the invention in a manner known per se, for example by means of solvolysis, in particular hydrolysis, alcoholysis, aminolysis, hydrazinolysis or acidolysis, by means of reduction, in particular hydrogenolysis, by means of photolysis or with the aid of enzymatic methods; with simultaneous elimination of all the protecting groups present or stepwise elimination, it being possible for intermediates which are partly freed from protecting groups to be further used in the non-purified or purified form. The elimination of the protecting groups is described, for example, in the abovementioned standard works.

The amino-protecting group(s) is/are preferably split off in a manner known per se, stepwise or simultaneously, depending on the nature of the protecting group(s), for example by means of reduction or solvolysis, in particular hydrolysis, preferably in an acid medium, alcoholysis, acidolysis, aminolysis or hydrazinolysis. Lower alkoxycarbonyl, such as the ten-butyloxycarbonyl group, or the trityl radical can be liberated, for example, by treatment with an acid, such as a mineral acid, for example sulfuric acid or a hydrogen halide acid, such as hydrochloric acid, in the presence or absence of solvents, in particular alcohols, such as methanol or ethanol, or ethers, such as tetrahydrofuran or diethyl ether, or an organic acid, for example formic, acetic or trifluoroacetic acid, in the presence or absence of water or an organic solvent, for example methylene chloride, at preferred temperatures of −20° C. up to the reflux temperature, in particular at 0° C. to room temperature or at the reflux temperature. Primary lower alkoxycarbonyl is preferably liberated under alkaline conditions, for example using hydroxy bases, such as alkali metal hydroxides, for example sodium hydroxide or potassium hydroxide, in water, aqueous solvents, such as alcohol/water mixtures, for example ethanol/water or methanol/water, or in alcohols, such as methanol or ethanol, at preferred temperatures as defined for acid splitting off of lower alkoxycarbonyl. The unsubstituted or substituted benzyloxycarbonyl group is split off, for example, reductively by hydrogenolysis, i.e. by treatment with hydrogen in the presence of a suitable catalyst, for example palladium, or by means of sodium in liquid ammonia, or by acidolysis, in particular by means of hydrogen bromide/glacial acetic acid. 2-Halo-lower alkoxycarbonyl can be split off, for example, by treatment with a suitable reducing agent, such as zinc, in the presence of an organic solvent, such as methanol or aqueous acetic acid. Lower alkyl-formimidoyl, such as tert-butylformimidoyl, is preferably split off by bases, such as hydroxides, in particular alkali metal hydroxides, for example potassium hydroxide. The hydrocarbyldicarboxylic acid radicals, in particular the phthaloyl group, can be split off, for example, by means of hydrazinolysis, for example with hydrazine hydrate in the presence or absence of organic solvents, such as alcohols, for example ethanol, or ethers, such as diethyl ether, at preferred temperatures of between 0° C. and the reflux temperature, for example at 20° to 30° C. or at the reflux temperature, by means of aminolysis, for example with primary amines, such as lower alkylamines, for example butylamine, cycloalkylamines, for example cyclohexylamine, or arylamines, such as aniline, or by means of ammonium salts, preferably in polar solvents, such as alcohols, for example methanol or ethanol, or (if ammonium hydroxide is used as the base) in water, at preferred temperatures of 50° C. to the reflux temperature, in particular at the reflux temperature, or by means of an acid, in particular a mineral acid, for example sulfuric acid or a hydrogen halide acid, such as hydrochloric acid, in water in the presence or absence of organic solvents, for example alcohols, such as methanol, at preferred temperatures of between 50° C. and the reflux temperature, in particular at the reflux temperature. Unsubstituted or substituted benzoyl is preferably split off under alkaline or acid conditions, for example with hydroxide bases, such as alkali metal hydroxides, for example sodium hydroxide or potassium hydroxide, in water or aqueous solvents, such as water/alcohol mixtures, for example water/ethanol or water/methanol, at preferred temperatures of between 50° C. and the boiling temperature of the reaction mixture, in particular at the reflux temperature, or in the presence of sulfuric acid or hydrogen halide acids, such as hydrochloric acid, in water or aqueous solvents, such as water/alcohol mixtures, for example water/methanol or water/ethanol, at preferred temperatures, as described for the liberation in the presence of hydroxide bases. For liberation of lower alkanoyl protecting groups, alkaline hydrolysis is preferably used, for example by means of hydroxy bases, such as alkali metal hydroxides, for example sodium hydroxide or potassium hydroxide, in water or aqueous solutions at preferred temperatures of 50° C. up to the reflux temperature, for example at the reflux temperature. Sulfo (including in salt form) is preferably removed by being split off under acid conditions, in particular with sulfuric acid or hydrogen halide acids, such as hydrochloric acid, in water or aqueous solvents, at preferred temperatures of between 50° C. and the reflux temperature, for example in the context of steam distillation. 1-Lower alkyl-lower alkylidene is preferably split off under acid conditions, for example in the presence of sulfuric acid or a hydrogen halide acid, such as hydrochloric acid, in water or an aqueous solvent at preferred temperatures of between 50° C. and the boiling point of the reaction mixture, for example under reflux or steam distillation. 1-Lower alkoxy-lower alkylidene is preferably liberated by reaction in the presence of acids, such as sulfuric acid or hydrogen halide acids, for example hydrochloric acid, in organic solvents, such as ethers, for example diethyl ether, in the presence of water at preferred temperatures of between 0° and 50° C., in particular at room temperature.

A hydroxyl group protected by a suitable acyl group or by unsubstituted or substituted 1-phenyl-lower alkyl is liberated analogously to a correspondingly protected amino group. A hydroxyl group protected by 2,2-dichloroacetyl is liberated, for example, by basic hydrolysis, and a hydroxyl group protected by tert-lower alkyl or by a 2-oxa- or 2-thia-aliphatic or-cycloaliphatic hydrocarbon radical is liberated by acidolysis, for example by treatment with a mineral acid or a strong carboxylic acid, for example trifluoroacetic acid.

Two hydroxyl groups or an adjacent amino and hydroxyl group which are protected together by means of a bivalent protecting group, preferably, for example, a methylene group which is mono- or disubstituted by lower alkyl, such as by lower alkylidene, for example isopropylidene, cycloalkylidene, for example cyclohexylidene, or benzylidene, can be liberated by acid solvolysis, in particular in the presence of a mineral acid or a strong organic acid.

Tri-lower alkylsilyl, such as trimethylsilyl or dimethyl-(2,3-dimethyl-2-butyl)silyl, is preferably split off by solvolysis, for example with alcohols, such as methanol or ethanol, at temperatures between 20° C. and the reflux temperature. A tri-lower alkylsilyl group is also split off by acidolysis with a mineral acid, preferably hydrofluoric acid, or a strong carboxylic acid, or by reaction with the fluoride salt of a metal or a base which liberates fluoride ions, for example the acid addition salt of hydrogen fluoride and a nitrogen base or a metal fluoride, such as an alkali metal fluoride, for example sodium fluoride or potassium fluoride, if appropriate in the presence of a macrocyclic polyether ("crown ether"), or with a fluoride of an organic quaternary base, such as tetra-lower alkylammonium fluoride or tri-lower alkylaryl-lower alkylammonium fluoride, for example tetraethylammonium fluoride or tetrabutylammonium fluoride, in the presence of aprotic, polar solvents, such as ethers, for example tetrahydrofuran or dioxane, dimethyl sulfoxide or N,N-dimethylacetamide, at preferred temperatures of about −20° to 50° C., for example between 0° C. and room temperature.

2-Halo-lower alkoxycarbonyl as the hydroxyl-protecting group is removed by reducing agents, for example reducing metal, such as zinc, reducing metal salts, such as chromium(II) salts, or by sulfur compounds, for example sodium dithionite or, preferably, sodium sulfide and carbon disulfide.

Esterified hydroxyl groups, for example lower alkanoyloxy, such as acetyloxy, can also be liberated by esterases, for example acylated amino can be liberated by suitable peptidases.

The starting materials of the formula II can be prepared by processes known per se, for example analogously to the methods described in Houben-Weyl, Methoden der Organischen Chemie [Methods of Organic Chemistry], Volume X/1 (1971) and Volume E 16a (1990).

The compounds of the formula II are preferably prepared from starting materials of the formula III

$X_1X_2N$—$(CR_1R_2)$—$(CR_3R_4)$—$(CR_5R_6)$—$W_1$    (III)

in which $R_1$, $R_2$, $R_3$, $R_4$, $R_5$ and $R_6$ are as defined for compounds of the formula I, $X_1$ and $X_2$ independently of one another are hydrogen or a monovalent amino-protecting group, with the proviso that at least one of the radicals $X_1$ and $X_2$ is an amino-protecting group, or $X_1$ and $X_2$ also together can form a bivalent protecting group, and $W_1$ is hydroxyl or a leaving group, or salts thereof; by reaction with a hydroxylamine of the formula IV

$X_3X_4N$—OH    (IV)

in which $X_3$ and $X_4$ have the meanings given for compounds of the formula II, and in which other functional groups in the starting materials which are not to participate in the reaction, in particular i.e. the hydroxyl groups in one of the radicals $R_1$, $R_2$, $R_3$, $R_4$, $R_5$ and $R_6$, are present in protected form if necessary.

In a compound of the formula III, a radical $W_1$ is hydroxyl or a leaving group, preferably a derivatitized hydroxyl group, for example sulfonyloxy substituted by aliphatic or aromatic substituents, such as lower alkanesulfonyloxy, for example methanesulfonyloxy, or arylsulfonyloxy (=aryl—$SO_2$—O—), in which aryl has 6 to 14 carbon atoms, preferably as phenyl, naphthyl, indenyl or indanyl, and is unsubstituted or substituted by up to three radicals, for example by lower alkyl, such as methyl, lower alkoxy, such as methoxy, or halogen, such as fluorine, chlorine or bromine, for example lower alkylphenylsulfonyloxy (=lower alkylphenyl—$SO_2$—O—), such as p-toluenesulfonyloxy, a substituted lower alkanesulfonyl group, such as halo-lower alkanesulfonyl, for example trifluoromethanesulfonyl, or, in particular, a free hydroxyl group or a halogen atom, for example chlorine, bromine or iodine.

If $W_1$ is hydroxyl, which is the case in a preferred embodiment of the preparation process of the compound of the formula II, the reaction is preferably carried out by an intramolecular dehydration reaction. A particularly suitable reaction is a variant of the Mitsunobu reaction (analogous to Synthesis, 682 (1976)), in which the compound of the formula III is reacted with an amino-protecting hydroxylamine of the formula IV, as defined above, in which the amino function is preferably protected by one of the above-mentioned bivalent amino-protecting groups, for example N-hydroxyphthalimide, N-hydroxy-5-norbornene-2,3-dicarboxylic acid imide or acetohydroxamic acid ethyl ester, in particular N-hydroxyphthalimide, and triarylphosphine, in which aryl preferably has 6 to 14 carbon atoms and is mono-, bi- or tricyclic, such as phenyl, naphthyl, indenyl or indanyl, for example triphenylphosphine, and an N,N'-azodicarboxylic acid diester, such as an N,N'-azodicarboxylic acid di-lower alkyl ester, for example diethyl N,N'-azodicarboxylate, preferably in an aprotic solvent, such as an ether, for example a cyclic ether, such as tetrahydrofuran, or, in particular, an aromatic solvent, such as benzene, toluene or xylene, without an inert gas or under an inert gas, such as nitrogen or argon, and at preferred temperatures of from 0° C. to 80° C., in particular from 10° to 40° C., for example at 20° to 30° C. The reaction is preferably earned out such that inversion takes place on the carbon atom carrying the hydroxyl group.

The reaction results in an aminooxy group protected by a bivalent amino-protecting group, in particular a hydrocarbyldicarboxylic acid radical bonded via both carbonyl groups, in a compound of the formula II which is obtainable.

Hydroxyl $W_1$ can also be convened into lower alkoxycarbonylaminoxy by nitrene insertion by reaction of N-carbonic acid lower alkyl ester-azides, such as carbonic acid ethyl ester-azide ($H_5C_2$—O—(C=O)—$N_3$), in organic solvents, for example carboxylic acid amides, such as dimethylformamide, or ethers, such as di-lower alkyl ethers, for example diethyl ether, at temperatures between 20° C. and the reflux temperature, preferably at the reflux temperature.

If $W_1$ is a derivatized hydroxyl as defined above, in particular a halogen atom, for example a bromine atom, or arylsulfonyl, such as toluenesulfonyl, the reaction is preferably carried out with an amino-protected hydroxylamine of the formula IV in which $X_3$ and $X_4$ together are the hydrocarbyldicarboxylic acid radical bonded via both carbonyl groups or a mono- or disubstituted methylidene group, as defined above, in particular 1-lower alkyl-alkylidene or 1-lower alkoxy-lower alkylidene; and in which $X_3$ is sulfo and $X_4$ is sulfo; or in which one of the radicals $X_3$ and $X_4$ is hydrogen and the other is an acyl group, as defined above, in particular lower alkoxycarbonyl, benzyloxycarbonyl, 2-halo-lower alkoxycarbonyl, lower alkyl-formimidoyl, unsubstituted or substituted benzoyl, lower alkanoyl or sulfo. The reaction of the compound of the formula III (which is preferably used directly, i.e. without further isolation), with the compound of the formula IV in this case is preferably carried out in an organic solvent, such as an aromatic solvent, for example benzene, toluene or xylene, in alcohols, such as lower alkanols, for example methanol or ethanol, in polar solvents, such as di-lower alkyl-carboxylic acid amides, for example dimethylformamide, di-lower alkyl sulfoxides, such as dimethyl sulfoxide, nitriles, such as acetonitrile, ketones, such as di-lower alkyl ketones, for example acetone, or ethers, such as cyclic ethers, for example tetrahydrofuran or dioxane, water (if necessary in the presence of detergents, for example Zephirol® (=benzyl-dodecyl-dimethyl-ammonium chloride and homologues, which contain other alkyl radicals instead of dodecyl; Bayer, Federal Republic of Germany)), or mixtures of the solvents mentioned, anhydrous conditions or the absence of protic solvents being preferred if the reaction is impaired too greatly by water or protic solvents (for example because of hydrolysis or solvolysis of the reagents); in the absence or presence of basic reagents or of catalysts, in particular of bases, for example carbonate or bicarbonate salts, such as alkali metal carbonates, for example potassium carbonate or bicarbonate or sodium carbonate or bicarbonate (if necessary in the presence of crown ethers, such as dibenzo-18-crown-6), alkali metal hydrides, such as sodium hydride, alkali metal amides, such as sodium amide, alkali metal alcoholates, such as sodium methoxide or sodium ethoxide (which can also be prepared in situ by addition of an alkali metal to the alcohol in question), sterically hindered amines, such as tertiary amines, for example triethylamine, N,N,N',N'-tetramethyl-methylenediamine or 1,8-diazabicyclo[5.4.0]undec-7-ene(1, 5–5), hydroxides, such as alkali metal hydroxides, for example sodium hydroxide or potassium hydroxide, or without bases, by employing the salts of the compounds of the formula IV directly or preparing them in situ (for example by addition of an alkali metal, such as sodium or potassium); at preferred temperatures of between 0° C. and the reflux temperature or with evaporation, in particular at 20° C., 40° to 80° C., at the reflux temperature or with evaporation; with or without an inert gas, such as argon or nitrogen, it being possible for the expert to select the particular suitable conditions.

The compounds of the formula II can also be prepared in a similarly preferred manner analogously from compounds of the formula III*

$$W_2-(CR_1R_2)-(CR_3R_4)-(CR_5R_6)-O-NX_3X_4 \qquad (III^*)$$

in which $R_1$, $R_2$, $R_3$, $R_4$, $R_5$ and $R_6$ are as defined for compounds of the formula I, $W_2$ is one of the radicals as defined for $W_1$ under formula III, in particular hydroxyl, $X_3$ and $X_4$ are as defined for compounds of the formula IV and hydroxyl groups which are not to participate in the reaction are present in protected form if necessary, as described above;

by reaction with an amine of the formula VII $$X_1X_2NH \qquad (VII),$$

as defined below, under conditions analogous to those described above for the reaction of compounds of the formula III with those of the formula IV, and if desired by subsequent splitting off of hydroxyl-protecting groups.

A preferred process for the preparation of compounds of the formula I starts from the compounds of the formula III or III* mentioned, which are reacted with the corresponding compounds of the formula IV or VII respectively under the conditions mentioned to give compounds of the formula II, which are then preferably converted into corresponding compounds of the formula I by splitting off protecting groups, as described above—the substituents here are in each case as defined above.

The compounds of the formula III, III* and IV are known or commercially obtainable or can be prepared by processes known per se.

The compounds of the formula III can be prepared, for example, by processes analogous to those described in Houben-Weyl, Methoden der organischen Chemie [Methods of Organic Chemistry], Volume X/1 (1971) and Volume E 16a (1990). In particular, they are prepared as follows:

Preferably, compounds of the formula V $$H_2N-(CR_1R_2)-(CR_3R_4)-(CR_5R_6)-W_1 \qquad (V)$$

in which $W_1$ is hydroxyl and the other radicals are as defined for compounds of the formula III (these compounds correspond to compounds in which, in the formula III, $W_1$ is hydroxyl, $X_1$ and $X_2$ are replaced by hydrogen atoms and the other radicals are as defined for compounds of the formula III)

are converted into compounds of the formula III in which $W_1$ is hydroxyl by reaction with reagents which introduce protecting groups $X_1$ and/or $X_2$ under conditions as are described in the abovementioned standard works or below for introduction of protecting groups during preparation of compounds of the formula IV (in which $X_3$ or $X_3'$ and $X_4$ or $X_4'$ in each case is to be replaced by $X_1$or, respectively, $X_2$ in the starting compounds).

Protecting groups, in particular amino- and hydroxyl-protecting groups, are introduced into the starting materials by methods known per se if necessary. Examples of suitable reaction conditions are described, for example, in the standard works by J. F. W. McOmie, "Protective Groups in Organic Chemistry", Plenum Press, London, N.Y., 1973, and T. W. Greene, "Protective Groups in Organic Synthesis", Wiley, N.Y., 1984.

For example, acyl groups $X_1$ or $X_2$ are introduced by customary methods for acylation of amino groups and for introduction of protecting groups, as described, for example, in the abovementioned standard works.

A particularly preferred preparation is that of those compounds of the formula III in which one of the radicals $X_1$ and $X_2$ is hydrogen and the other is a radical of an acyl radical of a carbonic acid half-ester, in particular lower alkoxycarbonyl, such as tert-butoxycarbonyl, or benzyloxycarbonyl, and the other radicals are as defined, from compounds of the formula V by reaction of an activated acid derivative of the formula VI

$$Y-W_2 \qquad (VI)$$

in which

Y is the acyl radical of a carbonic acid half-ester, in particular lower alkoxycarbonyl or benzyloxycarbonyl, while $W_2$ is a reactively derivatized hydroxyl group, preferably azolido, such as imidazolido, halogen, such as chlorine or bromine, or, in particular, an acyl radical, bonded via oxa, of a carbonic acid half-ester which is identical to Y (the compound of the formula VI is then a symmetric acid anhydride, i.e. a diester of dicarbonate).

The activated acid derivative of the formula VI can also be prepared in situ, for example by reaction in the presence of carbodiimides, for example N,N'-di-lower alkyl- or N,N'-di-$C_5$–$C_7$cycloalkylcarbodiimide, such as diisopropylcarbodiimide or N,N'-dicyclohexylcarbodiimide, advantageously in the presence of an activation catalyst, such as N-hydroxysuccinimide or N-hydroxybenzotriazole which is unsubstituted or substituted by halogen, lower alkyl or lower alkoxy.

The reaction is preferably carried out in an inert solvent, such as an ether, for example an aliphatic ether, such as diethyl ether, or a cyclic ether, such as tetrahydrofuran or dioxane, a liquid chlorinated hydrocarbon, such as methylene chloride or chloroform, or an N,N-di-lower alkyl-lower alkanecarboxylic acid amide, such as dimethylformamide, or mixtures thereof; it also being possible for water to be present, in particular if cyclic ethers or N,N-di-lower alkyl-lower alkanecarboxylic acid amides are used; at temperatures of between 0° C. and the reflux temperature, preferably between 15° and 75° C., for example at room temperature. Bases, for example tertiary amines, such as triethylamine, diisopropylethylamine, 4-dimethylaminopyridine, N-methylmorpholine or pyridine, are added if necessary.

Compounds of the formula V are commercially obtainable or known or can be prepared by processes known per se.

For example, a compound of the formula V,
in which
$R_1$ and $R_2$ are $C_1$–$C_2$alkyl or hydrogen, but preferably only one of these two radicals is $C_1$–$C_2$alkyl, and the other is hydrogen;
$R_3$ is hydrogen or, if either $R_1$ or $R_2$; or $R_1$ and $R_2$ are hydrogen, is $C_1$–$C_2$alkyl, preferably hydrogen;
$R_4$, $R_5$ and $R_6$ are hydrogen and
$W_1$ is hydroxyl,
is reacted by addition of primary or secondary nitrogen compounds of the formula VII $$X_1X_2\text{—NH} \qquad (VII)$$

in which
$X_1$ and $X_2$ are as defined, in particular one of the two radicals is hydrogen and the other is phenyl-lower alkyl-methyl, such as (R,S)-, (R)- or, in particular, 1(S)-phenylethyl, onto olefins of the formula VIII $$R_1R_2C\text{=}CR_3\text{—}COOC_nH_{2n+1} \qquad (VIII)$$

in which
the radicals are as just defined and
n is from 1 to 7 inclusive (where $C_nH_{2n+1}$ can also be branched), in particular n=1 or 2, (preferably in an alcohol, such as ethanol, under reflux conditions),
a resulting ester of the formula IX $$X_1X_2N\text{—}(CR_1R_2)\text{—}CHR_3\text{—}COOC_nH_{2n+1} \qquad (IX)$$

in which
the radicals are as defined last,
is reacted with a complex hydride, in particular lithium aluminium hydride or lithium-tris(tert-butoxy)-aluminium hydride, in an ether, such as an acyclic ether, for example diethyl ether, or a cyclic ether, such as tetrahydrofuran, preferably without the presence of water, or with sodium borohydride in the presence of LiCl in diols, such as digylcol, at temperatures of between 0° C. and the reflux temperature, for example between 20° C. and the reflux temperature, and the alcohol obtainable, of the formula Va $$X_1X_2N\text{—}(CR_1R_2)\text{—}CHR_3\text{—}CH_2\text{—}OH \qquad (Va)$$

in which
the radicals are as defined,
if desired is convened into the corresponding compound of the formula V by splitting off the protecting groups (or, since this is a compound of the formula III in which $W_1$ is hydroxyl, is further reacted directly as described above). If $X_1$ is, for example, phenyl-lower alkyl-methyl, such as 1(S)-phenylethyl, the splitting off is effected, for example, by hydrogenation, for example with hydrogen in the presence of a noble metal catalyst, such as palladium, which can be bonded to a support, such as aluminium oxide, silica gel, barium sulfate, strontium sulfate, calcium carbonate or charcoal, in an alcohol, such as a lower alkane hydroxide, for example ethanol, at temperatures of from 0° C. up to the reflux temperature, for example at about 50° C., preferably under normal pressure. If a centre of asymmetry exists in one of the radicals $X_1$ or $X_2$ and this radical is enantiomerically pure, for example in (S)-phenyl-lower alkyl-methyl, such as 1(S)-phenyl-ethyl, diastereomers of the formula Va or IX can be used in order to obtain enantiomerically pure compounds of the formula V after separation of the diastereomers, for example by chromatography on silica gel with organic solvent mixtures, such as (benzene or toluene)/(diethyl ether or dioxane)/(di-lower alkyl ketone, such as acetone), and accordingly a) after reduction of the ester group of a corresponding compound of the formula IX to give one of the formula Va and elimination of the optically active protecting group as described above; or b) elimination of the optically active protecting group, as described above, from a compound of the formula Va.

Compounds of the formula V
in which
$R_2$ is hydrogen,
$W_I$ is hydroxyl and
the other radicals are as defined for compounds of the formula V,
and in which hydroxyl groups present (apart from $W_1$) can also be in protected form, are split reductively, for example by reaction of isoxazolines of the formula X $$\begin{array}{c} R_1 \diagdown \phantom{xx} R_3 \\ \phantom{xx}\vert\vert \phantom{xxx} R_4 \\ N \diagdown \phantom{xxx} R_5 \\ \phantom{xxx} O \phantom{xx} R_6 \end{array} \qquad (X)$$

in which
$R_1$, $R_3$, $R_4$, $R_5$ and $R_6$ are as defined for compounds of the formula I, with a suitable complex hydride, such as lithium aluminium hydride, in an inert solvent, such as an ether, for example diethyl ether, at temperatures of between 0° C. and the reflux temperature, preferably at the reflux temperature, a corresponding compound of the formula V being obtained directly.

Compounds of the formula V
in which $R_1$ and $R_2$ independently of one another are methyl or ethyl, while $R_3$, $R_4$, $R_5$ and $R_6$ are hydrogen, and in which $W_1$ is hydroxyl, can be prepared, for example, by reaction of acrylic acid derivatives of the formula XI $$R_1R_2C=CHCOOH \qquad (XI)$$

in which $R_1$ and $R_2$ are $C_1$–$C_2$alkyl, with ammonia, preferably with concentrated aqueous ammonia, under increased pressure, for example under $1.5 \times 10^5$ to $100 \times 10^5$ Pa, in particular under about $40 \times 10^5$ to $60 \times 10^5$ Pa, at temperatures of 100° to 150° C., in particular at about 150° C., and subsequent reduction of the resulting compound of the formula XII $$R_1R_2C(-NH_2)-CH_2-COOH \qquad (XII)$$

in which the radicals are as defined, for example by hydrogenation with a complex hydride, such as lithium aluminium hydride, in inert organic solvents, in particular ethers, such as di-lower alkyl ethers, for example diethyl ether, or cyclic ethers, such as tetrahydrofuran, at preferred temperatures of between 35° C. and the boiling point of the reaction mixture, for example under reflux.

Compounds of the formula V in which $R_5$ and $R_6$ independently of one another are hydrogen or $C_1$–$C_2$alkyl, preferably methyl, with the proviso that only not more than one of these radicals can be hydrogen, and in which $R_1$, $R_2$, $R_3$ and $R_4$ are hydrogen and in which $W_1$ is hydroxyl, can be prepared, for example, by reduction of nitriles of the formula XIII $$HO-(CR_5R_6)-CH_2-C\equiv N \qquad (XIII)$$

in which the radicals are as defined last, preferably with a complex hydride, such as lithium aluminium hydride, in an inert solvent, in particular an ether, such as di-lower alkyl ether, for example diethyl ether, at temperatures of between 10° C. and the reflux temperature, preferably at the reflux temperature.

It is also possible for compounds of the formula II protected by amino-protecting groups $X_1$ and/or $X_2$ to be prepared directly without having to proceed via intermediates of the formula V with a free amino group.

Compounds of the formula II in which one of the radicals $R_1$, $R_2$, $R_3$, $R_4$, $R_5$ and $R_6$, preferably one of the radicals $R_1$, $R_2$, $R_3$ and $R_4$, is hydroxymethyl while the other of these radicals are hydrogen, and in which $W_1$ is hydroxyl and in which the other radicals are as defined for compounds of the formula II, can be obtained, for example, from amino acid derivatives of the formula XIV $$X_1X_2N-(CHT_1)-(CHT_2)-T_3 \qquad (XIV)$$

in which one of the radicals $T_1$ and $T_2$ is carboxyl or lower alkoxycarbonyl and the other is hydrogen, and in which $T_3$ is likewise carboxyl, lower alkoxycarbonyl or hydroxymethyl, or in which $T_1$ and $T_2$ are hydrogen and $T_3$ is bis(lower alkoxycarbonyl)methyl;

and in which preferably at least one of the radicals $X_1$ or $X_2$ is an amino-protecting group, in particular the acyl radical of a carbonic acid half-ester, such as lower alkoxycarbonyl, for example tert-butoxycarbonyl, by selective reduction with a suitable complex hydride, in particular with lithium borohydride in an inert solvent, in particular an ether, such as a cyclic ether, for example tetrahydrofuran, at temperatures of between 0° C. and the reflux temperature, in particular at about 40° C. If desired, corresponding compounds of the formula V can be obtained from the obtainable compounds of the formula II by splitting off amino-protecting groups $X_1$ and/or $X_2$, and these compounds can be converted into compounds of the formula II by introduction of further protecting groups, as described, for example, for compounds of the formula IV.

Compounds of the formula III in which $X_1$ and $X_2$ together are a bivalent protecting group, as defined above, in particular the radical of a hydrocarbyldicarboxylic acid bonded via both carbonyl groups, such as the phthaloyl radical, and in which $W_1$ is hydroxyl and in which $R_1$ and $R_5$ are as defined for compounds of the formula I, except for hydroxymethyl, $R_4$ is $C_1$–$C_2$alkyl and $R_2$, $R_3$ and $R_6$ are in each case hydrogen, are prepared, for example, by reacting an olefin of the formula XV $$L-(CR_1R_2)-CR_4=CHR_6 \qquad (XV)$$

in which

L is a leaving group as defined for $W_1$ in compounds of the formula III, in particular halogen, such as chlorine or bromine, and the other radicals are as defined last, with a nitrogen base of the formula XVI $$X_a=NH \qquad (XVI)$$

in which $X_a$ is a bivalent amino-protecting group as described above for a compound of the formula III as formed together from $X_1$ and $X_2$, in particular with phthalimide, preferably as a metal salt, such as an alkali metal salt, of a compound of the formula XIX in which the hydrogen is replaced by the corresponding metal cation (for an n-fold positive charge of the metal cation 1/n mol of this metal cation per mol of the radical $X_a=N\ominus$ for charge compensation), for example the potassium or sodium salt; in an inert solvent, for example a di-lower alkyl-lower alkanoylamide, such as dimethylformamide, or 1,3-dimethyl-3,4,5,6-tetrahydro-2(1H)-pyrimidinone (DMPU); at preferred temperatures of from 50° C. up to the reflux temperature, for example at 90° to 100° C.; the leaving group L being replaced to give an olefin of the formula XVII $$X_a=N-(CR_1R_2)-CR_4=CHR_6 \quad (XVII)$$

in which the radicals are as defined last, and then converting this olefin into the corresponding compound of the formula III in which $X_1$ and $X_2$ together are as defined for $X_a$, by hydroboronation, for example with borane, preferably in stabilized form, such as borane/dimethyl sulfide complex, in an aprotic solvent, such as an ether, for example a cyclic ether, such as tetrahydrofuran or dioxane, at preferred temperatures of between –30° C. and 40° C., in particular at about 0° to 30° C., and subsequent oxidation and alkaline oxidation of the resulting borane compound, for example with hydrogen peroxide in the presence of a hydroxy base, such as an alkali metal hydroxide, for example sodium hydroxide or potassium hydroxide, in water or an aqueous solvent mixture, such as water/tetrahydrofuran.

Compounds of the formula III in which $W_1$ is a leaving group can be prepared, for example, from compounds of the formula III in which $W_1$ is hydroxyl by reaction with the corresponding nucleophiles, for example a sulfonyl halide, such as bromide or chloride, substituted by aliphatic or aromatic substituents, such as a lower alkanesulfonyl halide, for example methanesulfonyl chloride, or arylsulfonyl halide (for example aryl-$SO_1$—Cl; —Br), in which aryl has 6 to 14 carbon atoms, for example as phenyl, naphthyl, indenyl or indanyl, and is unsubstituted or substituted by up to three radicals, for example by lower alkyl, such as methyl, lower alkoxy, such as methoxy, or halogen, such as fluorine, chlorine or bromine, for example lower alkylphenylsulfonyl chloride (=lower alkylphenyl-$SO_2$—Cl), such as p-toluenesulfonyl chloride, a substituted lower alkanesulfonyl halide, such as halo-lower alkanesulfonyl chloride, for example trifluoromethanesulfonyl chloride, or a hydrogen halide acid, in particular hydrochloric, hydrobromic or hydriodic acid, if necessary in a suitable solvent, for example a halogenated hydrocarbon, such as chloroform, methylene chloride or dichloroethane, in the absence (for example if the hydrogen halide acids are used) or presence of a tertiary nitrogen base, such as a tri-lower alkylamine, for example triethylamine or ethyldiisopropylamine, pyridine or dimethylaminopyridine, at temperatures of between –78° C. and the reflux temperature, in particular from –5° to 30° C. The conditions mentioned are preferably suitable for introduction of the leaving groups $W_1$ apart from halogen. Halogen radicals can preferably be introduced by reaction of the corresponding compounds in which $W_1$ is sulfonyloxy substituted by aliphatic or aromatic substituents, with, for example, a halide, in particular a metal halide, for example a metal chloride, bromide or iodide, such as an alkali metal chloride, bromide or iodide or alkaline earth metal chloride, bromide or iodide, in suitable solvents, for example di-lower alkyl ketones, such as acetone, at preferred temperatures of from –20° C. up to the reflux temperature, for example at 10° to 30° C., if appropriate in the presence of copper, for example in small pieces or as a powder, in the case of iodides.

A preferred procedure for preparation of compounds of the formula III in which $W_1$ is chlorine or bromine, $R_5$ and $R_6$ are hydrogen and the other radicals are as defined, is here also the preparation of compounds of the formula XVIII $$X_1X_2N-(CR_1R_2)-(CR_3R_4)-CH_2-W_1^* \quad (XVIII),$$

in which $X_1$ and $X_2$ and $R_1$, $R_2$, $R_3$ and $R_4$ are as defined for compounds of the formula III, in particular $X_1$ and $X_2$ together are a bivalent phthaloyl radical, and in which $W_1^*$ is chlorine or bromine (these are compounds of the formula III in which $R_5$ and $R_6$ are hydrogen and $W_1$ is bromine or chlorine), by reaction of a compound of the formula XIX $$X_1X_2N-(CR_1R_2)-(CR_3R_4)-CH_2-OH \quad (XIX)$$

in which the radicals are as defined last (these are compounds of the formula III in which $R_5$ and $R_6$ are hydrogen and $W_1$ is hydroxyl) with an inorganic acid halide, such as thionyl chloride, thionyl bromide, phosphorus trichloride or -bromide or phosphorus pentabromide or -chloride, in an inert solvent, for example an aromatic hydrocarbon, such as benzene, toluene or xylene, at temperatures of between 60° C. and the reflux temperature, for example in toluene or xylene at 90° to 110° C.

Compounds of the formula III* can preferably be prepared by reacting compounds of the formula V*

$$W_2-(CR_1R_2)-(CR_3R_4)-(CR_5R_6)-W_1 \quad (V^*)$$

in which $W_1$ and $W_2$ are as defined for compounds of the formula III* and I respectively, in particular are each hydroxyl, and hydroxyl groups present are protected if necessary, with a hydroxylamine of the formula IV as defined above, under reaction conditions analogous to those mentioned above for the reaction of compounds of the formula III with those of the formula IV, and splitting off protecting groups present if desired.

The compounds of the formula IV can be prepared for example, as follows:

If $X_3$ or $X_4$ is a monovalent amino-protecting group, for example an acyl radical, as defined above, free hydroxylamine or a salt thereof can be prepared by reaction with the acid of the formula XX or XXI which results in the acyl radical $$X_3'-OH \quad (XX)$$

$$X_4'-OH \quad (XXI)$$

in which

X₃' and X₄' are acyl, as defined above as the amino-protecting group, or with an activated derivative thereof, which can also first be formed in situ, by customary methods for acylation of amino groups and for introduction of protecting groups, as described, for example, in the standard works mentioned above. If X₃' or X₄' is, for example, lower alkanoyl or unsubstituted or substituted benzoyl, the activated derivative, in which the hydroxyl group of the formula XX or XXI is replaced by an activated hydroxyl group, is, for example, acyloxy, in which acyl is preferably the same as X₃' or X₄', azido, azolido, such as imidazolido, halogen, such as chlorine or bromine, or nitrophenoxy, for example the corresponding acid anhydride, acid azide or acid halide, in particular the corresponding acid chloride. The preparation of an activated acid derivative in situ is carried out, for example, by reaction in the presence of carbodiimides, for example N,N'-di-lower alkyl- or N,N'-di-C₅–C₇cycloalkyl-carbodiimide, such as diisopropylcarbodiimide or N,N'-dicyclohexylcarbodiimide, advantageously in the presence of an activation catalyst, such as N-hydroxysuccinimide, or N-hydroxybenzotriazole which is unsubstituted or substituted by halogen, lower alkyl or lower alkoxy. Bases, for example tertiary amines, such as methylamine, diisopropylethylamine, dimethylaminopyridine, N-methylmorpholine or pyridine, are added if necessary. If X₃' or X₄' is the radical of a half-ester of carbonic acid, the hydroxyl group in X₃' or X₄' is preferably present in a compound of the formula XX or XXI as an activated hydroxyl group as defined above; in particular, the hydroxyl group is then replaced by halogen, such as chlorine or bromine, or an azolyl radical, such as imidazolyl.

Alkylformimidoyl radicals X₃ or X₄ are introduced into hydroxylamine, for example, by a method analogous to that described by Meyers, A. et al., in J. Am. Chem. Soc. 106, 3270 (1984); the ten-butylformimidoyl radical is introduced, for example, by reaction of the free hydroxylamine with N,N-dimethyl-N'-tert-butylformamidine in the presence of a catalytic amount of ammonium sulfate in toluene at the reflux temperature, or alternatively by reaction of ten-butylformamide with Et₃O⁺BF₄⁻ in methylene chloride at room temperature, addition of the amino compound and further reaction in the temperature range from room temperature to 40° C.

Hydroxylaminedisulfonic acid (X₃ and X₄=sulfo in compounds of the formula IV), and in particular its alkaline earth metal or ammonium salts, are prepared, for example, by reaction of a concentrated solution of an alkali metal nitrite with alkali metal hydrogen sulfate, or corresponding ammonium salts, and sulfur dioxide.

Arylmethyl X₃ and/or X₄ in compounds of the formula IV are introduced, for example, by reaction of hydroxylamine with arylmethyl halides, in particular arylmethyl chlorides or bromides, with nucleophilic replacement of the halogen atom, preferably by reaction in the presence of a tertiary amine, such as triethylamine or pyridine, in an aprotic solvent, such as an ether, for example tetrahydrofuran or dioxane, or a carboxylic acid amide, such as di-lower alkylformamide, for example dimethylformamide.

If X₃ and X₄ in compounds of the formula IV together are a bivalent amino-protecting group, the following preparation processes are preferred for preparation of these starting compounds:

Oxime derivatives of the formula IVa

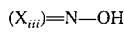

$(X_{iii})=N-OH$ (IVa)

in which $X_{iii}$ is a bivalent mono- or disubstituted methylidene group as defined above for compounds of the formula II in the case of X₃ and X₄, can be prepared from corresponding aldehyde or ketone intermediates in which =N—OH in formula IVa is replaced by a double-bonded oxygen (=O) under conditions customary for reaction of aldehydes or ketones with amino compounds, hydroxylamine, preferably as a salt, in particular with an inorganic acid, such as a hydrogen halide acid, for example hydrochloric acid, with sulfuric acid, for example as a sulfate or hydrogen sulfate, with phosphoric acid, for example as a phosphate, hydrogen phosphate or dihydrogen phosphate, with an organic acid, such as a lower alkanoic acid which is substituted in the lower alkyl radical by halogen, such as fluorine, chlorine or iodine, or is preferably unsubstituted, such as acetic acid, chloroacetic acid, dichloroacetic acid or trifluoro- or trichloroacetic acid, a sulfonic acid, such as a lower alkanesulfonic acid, for example methane- or ethanesulfonic acid or ethanedisulfonic acid, or with an aromatic sulfonic acid, such as benzene- or naphthalenesulfonic acid or naphthalene-1,5-disulfonic acid, or in the form of a double salt, such as Zn(NH₂OH)₂Cl₂ (Crismers reagent); being reacted with the corresponding aldehyde or ketone in water, an aqueous solvent mixture, such as mixtures of water with alcohols, for example methanol or ethanol, di-lower-alkyl sulfoxides, such as dimethyl sulfoxide, or di-lower alkyl-lower alkanoylamides, such as dimethylformamide, or in organic solvents, such as those mentioned last, or sufficiently inert nitriles, such as acetonitrile, mixtures thereof or liquid ammonia, preferably in aqueous-alcoholic solution, for example in methanol/water or ethanol/water, at temperatures of between −78° C. and the reflux temperature, preferably from −30° to 100° C., in particular from 5° to 90° C., for example at about 80° C.; under pressures of 1 to 10,000 bar, preferably under normal pressure if hydroxylamine salts are used; in the absence of a base or preferably, in the case of acid salts of the hydroxylamine, under buffering of the acid with a base, in particular a hydroxide, such as an alkali metal hydroxide, for example sodium hydroxide or potassium hydroxide, with a carbonate or bicarbonate, in particular an alkali metal carbonate or bicarbonate or alkaline earth metal carbonate or bicarbonate, for example sodium carbonate or potassium carbonate or sodium bicarbonate or potassium bicarbonate, with a salt of a weak organic acid, in particular an alkali metal salt of a lower alkanecarboxylic acid, for example sodium acetate or potassium acetate, with organic nitrogen bases, in particular sterically hindered (secondary or tertiary) amines, such as pyrrolidine, or pyridine, or with an anion exchanger, for example Amberlite® IR-4B, the presence of an alkali metal carbonate being particularly preferred. The compounds of the formula IVa in which $X_{iii}$ is 1-lower alkoxy-lower alkylidene, on the other hand, are obtainable, for example, analogously to the process accessible via Chem. Abstr. 73, 25359 and 66520 (1970).

Hydrocarbyldicarboxylic acid derivatives of the formula IVa, in which $X_{iii}$ is a hydrocarbyldicarboxylic acid radical bonded via both carbonyl groups as defined above for $X_3$ and $X_4$ in compounds of the formula II, can be prepared, for example, by reaction of hydroxylamine with the corresponding free hydrocarbyldicarboxylic acids which donate the hydrocarbyldicarbonyl radical, or reactive derivatives thereof. Reactive derivatives are, for example, the corresponding dicarboxylic acid anhydride, dicarboxylic acid diazide or dicarboxylic acid dihalide, in particular the corresponding dicarboxylic acid dichloride, or the corresponding inner dicarboxylic acid anhydride (the two carbonyl groups bonded via oxa), or reactive derivatives formed in situ, for example prepared as described above for compounds of the formula XX and XXI in the reaction with hydroxylamine. The reaction preferably takes place under conditions analogous to those described above for the reaction of the compounds of the formula XX and XXI. Transamination of the corresponding dicarboxylic acid diesters, such as dicarboxylic acid di-lower alkyl esters, for example dicarboxylic acid dimethyl or diethyl esters, with hydroxylamine is also possible.

The other starting materials are commercially obtainable or known or are prepared by processes known per se.

Additional process measures

Free compounds of the formula I obtainable by the processes defined and having salt-forming properties can be convened into their salts in a manner known per se; since these are basic compounds, this can be effected by treatment with acids or suitable derivatives thereof.

Compounds of the formula II furthermore can also be prepared from compounds of the formula I for purification purposes (for example for separation of enantiomers with the aid of protecting groups having a centre of asymmetry which is present in the pure form (for example in (S) or (R) configuration)). The purified compounds of the formula I are then liberated by splitting off the protecting groups, as described under process (a).

Isomer mixtures of compounds of the formula I which can exist in the form of several isomers can be separated into the individual isomers by processes known per se.

Mixtures of enantiomers, for example, can be separated into individual enantiomers, preferably by formation of salts with optically pure salt-forming reagents, such as (S,S)- or (R,R)-tartaric acid, (R)- or (S)-lactic acid, 1(R)- or 1(S)-camphorsulfonic acid or (L)-glutamic acid, and separation of the diastereomer mixture thus obtainable, for example by means of fractional crystallization, and/or enantiomer separation by mechanical harvesting, by introduction of optically active protecting groups which have centres of asymmetry, such as (S)-1-phenylethyl, and separation of the resulting diastereomers, for example by fractional crystallization, preferably chromatographically, for example by partition or adsorption chromatography, or by partition in multi-phase solvent mixtures, and elimination of the protecting groups as described above, or by chromatography on optically active column materials, such as optically active quartz, cellulose, optically active ion exchangers, D-dinitrobenzoylphenylglycine covalently bonded to aminopropyl-silica gel (Pirkle phase), D-3,5-dinitrobenzoylphenylglycine bonded to silica gel, or an enantiomerically pure amino acid, such as (L)-valine or (L)-proline, covalently bonded to silica gel, if expedient and appropriate, also in the form of a copper complex.

Starting materials which allow selective preparation of individual isomers of the compounds of the formula I, for example enantiomerically pure starting materials, in particular of the formula II, are preferably used directly.

Salts of free compounds of the formula I can be prepared in a manner known per se, for example by treatment with an acid, such as inorganic acid, for example hydrochloric acid or sulfuric acid, an organic carboxylic acid, for example adipic acid, or an organic sulfonic acid, for example benzenesulfonic acid, or with a suitable anion exchanger reagent which is charged, for example, with the anion of the corresponding acid. Salts can be convened into the free compounds in the customary manner, for example by treatment with a suitable basic agent, such as a hydroxy base in free solution, for example an alkali metal hydroxide, or such as an anion exchanger charged with hydroxide, for example by chromatography or by the batch process.

The conversion of a salt of a compound of the formula I can be carried out by preparation of the free compound and subsequent conversion thereof into an acid addition salt, as just described.

Direct conversion of an acid addition salt of one of the compounds of the formula I and an acid into an acid addition salt of the compound of the formula I and another acid with the second, new acid is also possible. This conversion is preferably carried out a) by reaction of the original acid addition salt in free solution in the presence of a suitable amount of the new acid, for example an excess, or b) on an anion exchanger charged with the anion of the new acid.

Gel chromatography salt conversion processes can also be used for all reactions which serve to convert acid addition salts of bases of the formula I into other acid addition salts or into the free compounds or the free bases into the corresponding acids.

The conversion of a salt, preferably a halide, such as chloride, into another salt, for example a salt of a doubly negatively charged acid, for example a sulfate, is to be preferred in particular if a crystalline salt of a compound of the formula I is thus obtained.

General reaction conditions

As a result of the close relationship between starting materials with salt-forming groups in the free form and in the form of salts and also as a result of the close relationships between compounds of the formula I in the free form and in the form of salts, the corresponding free compounds or their salts above and below are also to be understood, where expedient and appropriate, as meaning the corresponding salts or free starting materials or compounds of the formula I.

If there are acid groups in the starting materials, for example sulfo or carboxyl groups, for example, salts with bases, for example metal salts, such as alkali metal or alkaline earth metal salts, for example sodium, potassium, magnesium or calcium salts, ammonium salts and salts with nitrogen bases, such as quaternary nitrogen compounds, for example tetra-lower alkylammonium compounds, and the like, can exist. If basic groups are present, for example, salts can exist analogously to the acid addition salts mentioned in the definition of salts of the compounds of the formula I.

The compounds according to the invention with their salt-forming basic groups can be obtained in the free form or in the form of salts, depending on the procedure and reaction conditions.

The compounds, including their salts, can also be obtained in the form of their hydrates, or their crystals can include, for example, the solvent used for the crystallization. Hydrates can also first be formed from the resulting compounds, for example by leaving them to stand in air.

In the starting materials, functional groups which are not to participate in the reaction, in particular amino and hydroxyl groups, are present in protected form if necessary. The protected intermediates obtainable can be liberated or used further without splitting off protecting groups. The introduction and nature of the protecting groups used and their elimination here is analogous to that described above. An amino group can be present in a form protected by two protecting groups only within the context of what is possible chemically. Preferably, only one monovalent or only one bivalent protecting group is present on a protected amino group.

The abovementioned reactions can be carried out under reaction conditions known per se, in the absence (if the reagents, for example, themselves serve as solvents or are present as melts) or, usually, presence of solvents or diluents, preferably those which are inert towards the reagents used and dissolve or suspend these, in the absence or presence of catalysts, condensing agents or neutralizing agents, and, depending on the nature of the reaction and reaction participants, at reduced, normal or increased temperature, for example in the temperature range from about −80° C. to about 200° C., preferably about −20° C. up to the reflux temperature, for example at about 0° to 30° C. or at the reflux temperature, under atmospheric pressure or in a closed vessel, if appropriate under pressure, or in an inert atmosphere, for example under an argon or nitrogen atmosphere, if necessary with exclusion of light, the suitable parameters being chosen from those mentioned, where expedient and appropriate. The particular reaction conditions stated specifically are preferred.

Solvents and diluents are, for example, water, alcohols, for example lower alkyl hydroxides, such as methanol, ethanol or propanol, diols, such as ethylene glycol, triols, such as glycerol, or arylalcohols, such as phenol, acid amides, for example carboxylic acid amides, such as dimethylformamide or dimethylacetamide, or 1,3-dimethyl-3,4,5,6-tetrahydro-2(1H)-pyrimidinone (DMPU), or amides of inorganic acids, such as hexamethylphosphoric acid triamide, ethers, for example cyclic ethers, such as tetrahydrofuran or dioxane, or acyclic ethers, such as diethyl ether or ethylene glycol dimethyl ether, halogenated hydrocarbons, such as halo-lower alkanes, for example methylene chloride or chloroform, ketones, such as acetone, nitriles, such as acetonitrile, acid anhydrides, such as acetic anhydride, esters, such as ethyl acetate, bisalkanesulfines, such as dimethyl sulfoxide, heterocyclic nitrogen compounds, such as pyridine, hydrocarbons, for example lower alkanes, such as heptane, or aromatics, such as benzene, toluene or xylene(s), or mixtures of these solvents, it being possible for the particular suitable solvents to be chosen for the abovementioned reactions.

The customary processes are used for working up the compounds of the formula I which are obtainable or their salts, for example solvolysis of excess reagents; recrystallization; chromatography, for example, partition, ion or gel chromatography; partition between an inorganic and organic solvent phase; single or multiple extraction, in particular after acidification or increasing the basicity or the salt content; drying over hygroscopic salts; digestion; filtration; washing; dissolving; evaporation (if necessary in vacuo or under a high vacuum); distillation; crystallization, for example of resulting compounds in the form of an oil or from the mother liquor, it also being possible for the product to be seeded with a crystal of the end product; or a combination of two or more of the working-up steps mentioned, which can also be employed repeatedly, and the like.

Starting materials and intermediates can be used in the pure form, for example after working up, as mentioned last, in the partly purified form or also, for example, directly as the crude product.

If isomers are present, for example enantiomers, these can be separated at any stage, either at the stage of a starting material or at that of end products, in the abovementioned processes, or isomerically pure starting materials can be employed directly.

Processes analogous to the processes mentioned in the examples are particularly preferred for the preparation both of the starting materials and of the end products.

The invention also relates to those embodiments of the process in which a compound obtainable as an intermediate at any process stage is used as the starting substance and the missing process steps are carried out, or in which a starting material is formed under the reaction conditions or is used in the form of a derivative, for example a salt thereof.

Pharmaceutical compositions

The present invention also relates to pharmaceutical compositions which comprise, as the active ingredient, one of the pharmacologically active compounds of the formula I or a pharmaceutically acceptable salt thereof. Compositions for enteral, in particular oral, and for parenteral administration are particularly preferred. The compositions comprise the active ingredient by itself or, preferably, together with a pharmaceutically acceptable carrier. The dosage of the active ingredient depends on the disease to be treated and on the species, age, weight, skin area and indidividual condition, as well as on the mode of administration.

The pharmaceutical compositions comprise about 5% to about 95% of the active ingredient, single-dose administration forms preferably containing from about 20% to about 90% and administration forms which are not single-dosed preferably containing about 5% to about 20% of active ingredient. Dose units forms, such as coated tablets, tablets or capsules, contain from about 0.01 g to about 2 g, preferably from about 0.05 to about 1.0 g of the active ingredient, in particular from 0.1 to 0.6 g.

The present invention also relates to the use of compounds of the formula I for the preparation of pharmaceutical compositions for use as ODC inhibitors, for example for the treatment of diseases which respond to inhibition of ODC, in particular the abovementioned diseases.

The pharmaceutical compositions of the present invention are prepared in a manner known per se, for example by means of conventional mixing, granulating, coating, dissolving or lyophilizing processes. Thus, pharmaceutical compositions for oral use can be obtained by combining the active ingredient with one or more solid carriers, granulating a resulting mixture, if appropriate, and processing the mixture or granules, if desired, to tablets or coated-tablet cores, if appropriate by addition of additional excipients.

Suitable carriers are, in particular, fillers, such as sugars, for example lactose, sucrose, mannitol or sorbitol, cellulose preparations and/or calcium phosphates, for example tricalcium phosphate or calcium hydrogen phosphate, and furthermore binders, such as starches, for example corn, wheat, rice or potato starch, methylcellulose, hydroxypropylmethylcellulose, sodium carboxymethylcellulose and/or polyvinylpyrrolidone, and/or, if desired, disintegrants, such as the abovementioned starches, and furthermore carboxymethyl starch, crosslinked polyvinylpyrrolidone, alginic acid or a salt thereof, such as sodium alginate. Additional excipients are, in particular, flow conditioners and lubricants, for example silicic acid, talc, stearic acid or salts thereof, such as magnesium stearate or calcium stearate, and/or polyethylene glycol, or derivatives thereof.

Coated-tablet cores can be provided with suitable coatings, if appropriate resistant to gastric juice, the substances used being, inter alia, concentrated sugar solutions, which contain gum arabic, talc, polyvinylpyrrolidone, polyethylene glycol and/or titanium dioxide if appropriate, coating solutions in suitable organic solvents or solvent mixtures or, for the preparation of coatings which are resistant to gastric juice, solutions of suitable cellulose preparations, such as acetylcellulose phthalate or hydroxypropylmethylcellulose phthalate. Dyes or pigments can be admixed to the tablets or sugar coated tablet coatings, for example for identification or characterization of different active ingredient doses.

Pharmaceutical compositions which can be used orally are also dry-filled capsules of gelatin and soft, closed capsules of gelatin and a softener, such as glycerol or sorbitol. The dry-filled capsules can contain the active ingredient in the form of granules, for example mixed with fillers, such as corn starch, binders and/or lubricants, such as talc or magnesium stearate, and if appropriate stabilizers. In soft capsules, the active ingredient is preferably dissolved or suspended in suitable liquid excipients, such as fatty oils, paraffin oil or liquid polyethylene glycols, it also being possible to add stabilizers.

Further oral administration forms are, for example, syrups which are prepared in the customary manner and contain the active ingredient, for example, in suspended form and in a concentration of about 5% to 20%, preferably about 10%, or in a similar concentration which gives a suitable single dose, for example, when 5 or 10 ml are measured out. Further suitable forms are also, for example, pulverulent or liquid concentrates for preparation of shakes, for example in milk. Such concentrates can also be packed in single-dose amounts.

Pharmaceutical compositions which can be used used rectally are, for example, suppositories, which comprise a combination of the active ingredient with a suppository base. Suitable suppository bases are, for example, naturally occurring or synthetic triglycerides, paraffin hydrocarbons, polyethylene glycols or higher alkanols.

Compositions which are suitable for parenteral administration are, in particular, aqueous solutions of an active ingredient in water-soluble form, for example a water-soluble salt, or aqueous injection suspensions which contain viscosity-increasing substances, for example sodium carboxymethylcellulose, sorbitol and/or dextran, and if appropriate stabilizers. The active ingredient can also be present here in the form of a lyophilizate, if appropriate together with excipients, and can be dissolved by addition of suitable solvents before parenteral administration.

Solutions such as are used, for example, for parenteral administration can also be used as infusion solutions.

The invention also relates to a method (process) for the treatment of the abovementioned disease states in warm-blooded animals, i.e. mammals, and in particular humans, preferably those warm-blooded animals which require such treatment. The compounds of the formula I of the present invention or their pharmaceutical salts, if salt, forming groups are present, are administered for this purpose for prophylaxis or treatment, and are preferably used in the form of pharmaceutical compositions, for example in an amount which is suitable for inhibition of ornithine decarboxylase and is active prophylactically or therapeutically against one of the diseases mentioned which respond to inhibition of ornithine decarboxylase, for example tumours or protozoa infections. For a body weight of about 70 kg, a daily dose of about 0.3 g to about 15 g, preferably about 0.5 g to about 5 g, of a compound of the present invention is administered hem.

The pharmaceutical compositions are preferably those which are suitable for administration to a warm-blooded animal, for example a human, for treatment or prophylaxis of one of the abovementioned diseases which responds to inhibition of ornithine decarboxylase and comprise an amount of a compound of the formula I or of a pharmaceutically acceptable salt thereof which is active against diseases which respond to inhibition of ornithine decarboxylase (in particular an amount which is active for inhibition of this enzyme), together with an excipient.

The examples described below serve to illustrate the invention, without limiting the scope thereof.

The abbreviation BOC is the ten-butoxycarbonyl group. m.p. is "melting point" and decomp. is "with decomposition". Brine is sodium chloride solution saturated at room temperature. Ether is diethyl ether, acetic ester is ethyl acetate. Optical rotations of enantiomers are stated in degrees, followed by the concentration (in per cent by volume) in the particular solvent used for the measurement. Temperatures are stated in degrees Celcius. In the case of mixtures of solvents and diluents, the volume ratios are stated.

EXAMPLE 1

(2S)-4-Aminooxy-2-butylamine dihydrochloride

A mixture of 12.74 g (0.381 mol) of (3S)-N-[3-(N-BOC-amino)-butyl-1-oxy]-phthalimide and 100 ml of 6N hydrochloric acid is refluxed for 2 hours. The reaction mixture is then cooled to 5° C. and filtered, the residue on the filter is washed with water and the filtrate is evaporated in vacuo. After recrystallization of the residue from methanol/ether, the resulting crystals are dried under a high vacuum at 90° C. and then left to stand at 20° C. under room atmosphere for 24 hours. The title compound is thus obtained in the form of the monohydrate, m.p. 161°–163° C. (decomp.), $[\alpha]_D^{20}$=–1.7±0.5° (c=2%, H$_2$O).

The starting compounds are prepared as follows:
a) (3S)-N-[3-(N-BOC-amino)-butyl-1-oxy]-phthalimide A solution of 13 ml (0.07775 mol) of diethyl azodicarboxylate (93%) in 30 ml of benzene is added dropwise to a mixture of 13.98 g (0.0739 mol) of(3S)-(N-BOC-amino)-butan-1-ol, 12.07 g (0.0739 mol) of N-hydroxyphthalimide, 19.4 g (0.0739 mol) of triphenylphosphine and 200 ml of benzene at 20°–30° C., while stirring. The reaction mixture is stirred at room temperature for 2 hours and then evaporated in vacuo. The residue is purified by means of flash chromatography on silica gel of particle size 0.04–0.063 mm using methylene chloride and methylene chloride/acetic ester mixtures (20:1 and 10:1). After evaporation of the product-containing fractions and recrystallization of the residue from acetonitrile, the title compound is obtained, m.p. 147°–149° C., $[\alpha]_D^{20}$ =–15°±05° (c=2%, CHCl$_3$).
b) (3S)-(N-BOC-amino)-butan-1-ol A solution of 21.48 g (0.0984 mol) of di-tert-butyldicarbonate in 100 ml of tetrahydrofuran is added dropwise to a mixture of 8.2 g (0.092 mol) of (3S)-aminobutan-1-ol [J. Org. Chem. 42,1650 (1977)] in 80 ml of tetrahydrofuran and 25 ml of water and the mixture is stirred at room temperature for 8 hours. The reaction mixture is then evaporated in vacuo and the residue obtained as an oil is purified by means of flash chromatography on silica gel using acetic ester/hexane mixtures (1:3 and 1:1). After evaporation of the product-containing fractions, the title compound is obtained as a colourless oil, R$_f$ value=0.78 (silica gel/methylene chloride:methanol:concentrated ammonia (40:10:1)), $[\alpha]_D^{20}$=+16.6±0.4° (c=2%, ethanol).

EXAMPLE 2

(2R)-4-Aminooxy-2-butylamine dihydrochloride

Analogously to Example 1, starting from 18.49 g (0.0553 mol) of (3R)-N-[3-(N-BOC-amino)-butyl-1-oxy]-phthalimide and 150 ml of 6N hydrochloric acid, the title compound is obtained in the form of the monohydrate, m.p. 161°–163° C. (decomp.), $[\alpha]_D^{20}$=+1.3±0.5° (c=2%, H$_2$O).

The starting compounds are prepared as follows:

a) (3R)-N-[3-(N-BOC-amino)-butyl-1-oxy]-phthalimide

Analogously to Example 1a, starting from 14.55 g (0.07688 mol) of (3R)-(N-BOC-amino)-butan-1-ol, 12.54 g (0.07687 mol) of N-hydroxyphthalimide, 20.16 g (0.07686 mol) of triphenylphosphine, 250 ml of benzene and a solution of 13.51 ml (0.0808 mol) of diethyl azodicarboxylate (93%) in 30 ml of benzene, the title compound is obtained, m.p. 146°–148° C., $[\alpha]_D^{20}$=+14.1 ±0.5° (c=2%, CHCl$_3$).

b) (3R)-(N-BOC-amino)-butan-1-ol

Analogously to Example 1b, starting from 8.7 g (0.0976 mol) of (3R)-aminobutan-1-ol [J. Org. Chem. 42, 1650 (1977)] and 22.16 g (0.1015 mol) of di-tert-butyl dicarbonate, the title compound is obtained as a colourless oil which gradually crystallizes, m.p. 55°–57° C., $[\alpha]_D^{20}$=−17.7±0.5° (c=2%, ethanol)

EXAMPLE 3

4-Aminooxy-2-butylamine dihydrochloride

A mixture of 6.92 g (0.0207 mol) of N-[3-(N-BOC-amino)-butyl-1-oxy]-phthalimide and 30 ml of hydrazine hydrate is stirred at room temperature for 0.5 hour, 25 ml of water and 75 ml of ether are then added and stirring is continued for 1 hour. The organic phase is separated off, the aqueous phase is extracted thoroughly with water and the combined ether phases are washed with brine, dried over sodium sulfate and evaporated in vacuo. The residue is purified by means of flash chromatography on silica gel using acetic ester/hexane mixtures (1:1 and 2:1). After evaporation of the product-containing fractions, 3.7 g of crude 4-aminooxy-2-N-BOC-butylamine are obtained, $R_f$ value=0.33 (silica gel/acetic ester).

To split off the N-BOC protecting group, the intermediate is dissolved in 70 ml of 3N methanolic hydrochloric acid and the solution is left to stand at room temperature for 3 days. The reaction mixture is then evaporated in vacuo and the residue is recrystallized from methanol/ether. The title compound obtained after drying under a high vacuum melts at 149°–151° C. (decomp.) and absorbs 1 mol of water under room atmosphere, m.p. ≧83° C. (decomp. about 140° C.; monohydrate of the title compound).

The starting compounds are prepared as follows:

a) N-[3-(N-BOC-amino)-butyl-1-oxyl]-phthalimide

Analogously to Example 1a, starting from 15.14 g (0.08 mol) of 3-(N-BOC-amino)-butan-1-ol, 13.05 g (0.08 mol) of N-hydroxyphthalimide, 20.98 g (0.08 mol) of triphenylphosphine, 250 ml of benzene and a solution of 14.04 ml (0.084 mol) of diethyl azodicarboxylate (93%) in 30 ml of benzene, the title compound is obtained, m.p. 154°–155° C. (from ether).

b) 3-(N-BOC-amino)-butan-1-ol

A solution of 18.33 g (0.084 mol) of di-tert-butyl dicarbonate in 50 ml of methylene chloride is added dropwise to a solution of 7.13 g (0.08 mol) of 3-aminobutan-1-ol [Chem. Ber. 91, 2383 (1958)] in 50 ml of methylenchloride and the mixture is stirred at room temperature for 22 hours. The reaction mixture is then evaporated and the residue obtained as an oil is purified by means of flash chromatography on silica gel using methylene chloride. After evaporation of the product-containing fractions, the title compound is obtained as an oil, $R_f$ value=0.54 (silica gel/methylene chloride:methanol (9:1)).

EXAMPLE 4

1-aminooxy-3-pentylamine dihydrochloride

Analogously to Example 1, 2.5 g (0.007176 mol) of N-[3-(N-BOC-amino)-pentyl-1-oxy]-phthalimide are reacted in 20 ml of 6N hydrochloric acid. After recrystallization from methanol/acetonitrile, the hygroscopic rifle compound is obtained with a water content of 2.75%, m.p. 139°–141° C. (decomp.).

The starting compounds are prepared as follows:

a) N-[3-(N-BOC-amino)-pentyl-1-oxy]-phthalimide

A solution of 3.51 ml (0.021 mol) of diethyl azodicarboxylate (93%) in 5 ml of benzene is added dropwise to a mixture of 4.07 g (0.02 mol) of 3-(N-BOC-amino)-pentan-1-ol, 3.26 g (0.02 mol) of N-hydroxyphthalimide, 5.25 g (0.02 mol) of triphenylphosphine and 40 ml of benzene at 20°–30° C., while stirring. The reaction mixture is stirred at room temperature for 15 hours, subsequently cooled to 5° C. and filtered and the filtrate is evaporated in vacuo. The residue is purified by means of flash chromatography on silica gel using acetic ester/hexane mixtures (1:4 and 1:3). After evaporation of the product-containing fractions, the title compound is obtained as a crystalline residue, m.p. 118°–120° C.

b) 3-(N-BOC-amino)-pentan-1-ol

A solution of 14.2 g (0.065 mol) of di-tert-butyl dicarbonate in 30 ml of tetrahydrofuran is added dropwise to a solution of 6.1 g (0.05912 mol) of 3-amino-pentan-1-ol (Bull. Soc. Chim. France 1962, 2215)in 60 ml of tetrahydrofuran and the mixture is stirred at room temperature for 2 hours. The reaction mixture is then evaporated and the residue obtained as an oil is purified by means of flash chromatography on silica gel using acetic ester/hexane mixtures (1:3 and 1:2). After evaporation of the product-containing fractions, the title compound is obtained as an oil, $R_f$ value=0.86 (silica gel/methylene chloride:methanol:concentrated ammonia (40:10:1)).

EXAMPLE 5

4-Aminooxy-2-methyl-2- butylamine dihydrochloride

Analogously to Example 1, 2.787 g (0.008 mol) of N-[3-(N-BOC-amino)-3-methyl-butyl-1-oxy]-phthalimide in 20 ml of 6N hydrochloric acid are reacted. After crystallization from ethanol/ether, the title is obtained, m.p. 70°–72° C. (decomp.).

The starting compounds are prepared as follows:

a) N-[3-(N-BOC-amino)-3-methyl-butyl-1-oxyl]-phthalimide

A solution of 7.02 ml (0.042 mol) of diethyl azodicarboxylate (93%) in 10 ml of toluene is added dropwise to a mixture of 8.13 g (0.04 mol) of 3-(N-BOC-amino)-3-methyl-butan-1-ol, 6.53 g (0.04 mol) of N-hydroxyphthalimide, 10.49 g (0.04 mol) of triphenylphosphine and 150 ml of toluene at 20°–30° C., while stirring. The reaction mixture is treated analogously to Example 4a and purified by means of flash chromatography on silica gel using acetic ester/hexane mixtures (1:3 and 1:2). The title compound is obtained as an oil which gradually crystallizes, m.p. 129°–132° C.

b) 3-(N-BOC-amino)-3-methyl-butan-1-ol

A solution of 24.88 g (0.114 mol) of di-tert-butyl dicarbonate in 70 ml of methylene chloride is added dropwise to a solution of 11.2 g (0.1086 mol) of 3-amino-3-methyl-butan-1-ol [Z. Naturforsch., Teil B, 38, 1146 (1983)] in 70 ml of methylene chloride and the mixture is stirred at room temperature for 90 hours. After evaporation of the reaction mixture in vacuo, the oily title compound is obtained as a crude product, $R_f$ value=0.52 (silica gel/methylene chloride:methanol (9:1)).

EXAMPLE 6

(2S)-4-Aminooxy-1-hydroxy-2-butylamine sulfate

A mixture of 1.81 g (0.005166 mol) of (3S)-N-[3-(N-BOC-amino)-4-hydroxy-butyl-1-oxy]-phthalimide and 12 ml of hydrazine hydrate is stirred at room temperature for ½ hour, 12 ml of water and 75 ml of methylene chloride are then added and stirring is continued for 4 hours. The organic phase is separated off, the aqueous phase is extracted with methylene chloride and the combined methylene chloride phases are washed with brine, dried over sodium sulfate and evaporated in vacuo. The residue is purified by means of flash chromatography on silica gel using a tert-butyl methyl ether/methanol mixture (7:3). After evaporation of the product-containing fractions, 0.985 g of crude (2S)-4-aminooxy-2-(N-BOC-amino)-butan-1-ol is obtained as an oil, $R_f$ value=0.54 (silica gel/tert-butyl-methyl ether/methanol (7:3)).

To split off the N-BOC protecting group, the intermediate is stirred in a mixture of 10 ml of ether and 0.3 ml of 90% sulfuric acid at room temperature for 24 hours. The crystals thereby formed are filtered off and then suspended in hot (about 50° C.) methanol, while stirring. After cooling and filtration, the title compound is obtained, m.p. 207°–210° C. (decomp.), $[\alpha]_D^{20}$=+3.7±1.1° (c=0.92%, H$_2$O).

The starting compound is prepared as follows:

a) (3S)-N-[3-(N-BOC-amino)-4-hydroxy-butyl-1-oxy]-phthalimide

A solution of 3.85 ml (0.0234 mol) of diethyl azodicarboxylate (93%) in 17 ml of benzene is added dropwise to a mixture of 4.5 g (0.02194 mol) of (2S)-(N-BOC-amino)-1,4-butanediol (EP 0 352 123 A2, Example 19 (b) therein), 3.58 g (0.02194 mol) of N-hydroxyphthalimide, 5.75 g (0.02192 mol) of triphenylphosphine and 45 ml of benzene at 20°–30° C., while stirring. The reaction mixture is stirred at room temperature for 15 hours, subsequently cooled to 5° C. and filtered and the filtrate is evaporated in vacuo. The residue is suspended in ether and filtered off and the filtrate is evaporated in vacuo. The residue is purified by means of flash chromatography on silica gel using a tert-butyl methyl ether/hexane mixture (7:3). After evaporation of the product-containing fractions and recrystallization of the residue from ethanol/water, the title compound is obtained, m.p. 98°–99° C., $[\alpha]_D^{20}$=−10.0±1.8° (c=0.55%, ethanol).

EXAMPLE 7

3-Aminooxy-2-methyl-1-propylamine sulfate 2.6 g (0.0071356 mol) of N-[2-methyl-3-phthalimido-propyl-1-oxy]-phthalimide are dissolved in 17 ml of hydrazine hydrate, while stirring, 15 ml of water are added to the reaction mixture after 0.5 hour has expired, and stirring is continued at room temperature for 3 hours. After addition of 100 ml of methylene chloride, the reaction mixture is stirred for a further 0.5 hour and the organic phase is then separated off. The aqueous phase is extracted thoroughly with methylene chloride and the combined organic phases are dried over sodium sulfate and evaporated in vacuo. The residue obtained as an oil is dissolved in 5 ml of ethanol, and a solution of 0.4 ml of 96% sulfuric acid in 2 ml of ethanol is added. The mixture is stirred at 0° C. for ½ hour and the precipitate formed is filtered off and partitioned between 2N sodium hydroxide solution saturated with sodium chloride and methylene chloride. After repeated extraction with methylene chloride, the extract, which has been dried over sodium sulfate, is evaporated in vacuo. The residue obtained as an oil (free base of the title compound) is convened into the title compound by treatment with a solution of 96% surfuric acid in methanol, m.p. 234°–236° C. (decomp.).

The starting compounds are prepared as follows:

a) N-[2-Methyl-3-phthalimido-propyl-1-oxy]-phthalimide

A solution of 5.37 ml (0.0335 mol) of diethyl azodicarboxylate (93%) in 23 ml of benzene is added dropwise to a mixture of 7.0 g (0.0319 mol) of 2-methyl-3-phthalimido-propan-1-ol, 5.2 g (0.0319 mol) of N-hydroxyphthalimide, 8.37 g (0.0319 mol)of triphenylphosphine and 70 ml of benzene at 20°–30° C., while stirring. The reaction mixture is stirred at room temperature for 15 hours and filtered and the filtrate is evaporated in vacuo. After crystallization of the residue from methanol, the title compound is obtained, m.p. 138°–140° C.

b) 2-Methyl-3-phthalimido-propan-1-ol 6.83 ml of borane dimethylsulfide complex (BH$_3$ concentration about 10M; Fluka, Switzerland) are added dropwise to a solution, cooled to −5° C. of 25.1 g (0.1247 mol) of N-(2-methyl-2-propenyl)-phthalimide [J. Med. Chem. 22, 631 (1979)] in 250 ml of tetrahydrofuran, while stirring and under a nitrogen atmosphere. The mixture is stirred at −5° C. for 0.5 hour and at room temperature for 2.5 hours and cooled to −5° C. again, and a mixture of 12.9 ml of tetrahydrofuran and 5.8 ml of water, 37.5 ml (0.075 mol) of 2N sodium hydroxide solution and 18.37 ml (0.18 mol) of 30% hydrogen peroxide are then added dropwise in succession to the reaction mixture, it being ensured that the temperature does not exceed 0° C. The reaction mixture is further stirred for 0.5 hour, without cooling, and then poured into a solution, cooled to 10°, of 189.5 g of potassium carbonate in 237 ml of water. The mixture is extracted with acetic ester and the acetic ester extract is washed with brine, dried over sodium sulfate and evaporated in vacuo. The residue is purified by means of flash chromatography on silica gel using methylene chloride/methanol (20:1). After evaporation of the product-containing fractions, the title compound is obtained as a resinous residue, $R_f$ value=0.55 (silica gel/methylene chloride:methanol (9:1)).

EXAMPLE 8

(2S)-4-Aminooxy-2-butylamine dihydrochloride

A mixture of 1.03 g (0.00283 mol) of (3S)-N-(3-phthalimido-butyl-1-oxy)-phthalimide, 6 ml of water and 8 ml of concentrated hydrochloric acid is heated under reflux for 14 hours. The reaction mixture is then cooled to 5° C. and filtered, the residue on the filter is washed with water and the filtrate is evaporated in vacuo. After recrystallization of the residue from methanol/ether, the resulting crystals are dried in vacuo at 80° C. and then left to stand at room temperature under room atmosphere for 2 days. The title compound is obtained with a water content of 9.80%, m.p. 160°–162° C. (decomp.), $[\alpha]_D^{20}$=−1.6±0.3° (c=3.1%, H$_2$O).

The starting compounds are prepared as follows:

a) (3S)-N-(3-Phthalimido-butyl-1-oxy)-phthalimide 0.745 ml (0.005 mol) of 1,8-diazabicyclo[5.4.0]undec-7-ene (DBU) is added dropwise to a solution of 1.481 g (0.00525 mol) of (2S)-N-(4-bromobutyl)-phthalimide and 0.815 g (0.005 mol) of N-hydroxyphthalimide in 10 ml of dimethylformamide, while stirring, and stirring is then continued at room temperature for 3 hours. The reaction mixture is then evaporated in vacuo and the residue is partitioned between methylene chloride and water. The organic phase is dried over sodium sulfate and evaporated in vacuo. After recrystallization of the residue from ethanol, the title compound is obtained, m.p. 135°–136° C., $[\alpha]_D^{20}=18.0\pm0.30°$ (c=3%, CHCl$_3$).

b) (2S)-N-(4-Bromobutyl)-phthalimide

A well-stirred mixture of 5.35 g (0.06 mol) of (3S)-aminobutan-1-ol, 8.89 g (0.06 mol) of phthalic anhydride and 50 ml of toluene is refluxed, using a water separator, at a bath temperature of 140° C. for 3 hours. The heating bath is then removed and a solution of 3.7 ml (0.0394 mol) of phosphorus tribromide in 4 ml of toluene is added dropwise to the hot reaction mixture, which contains (2S)-N-(4-hydroxybutyl)-phthalimide intermediately formed. The mixture is then stirred at 100° C. for a further ½ hour and the hot solution is then decanted from the somewhat oily precipitate and evaporated in vacuo. After recrystallization of the residue from isopropanol/water, the title compound is obtained, m.p. 55°–57° C., $[\alpha]_D^{20}=+46.4\pm0.3°$ (c=3%, C$_2$H$_5$OH).

EXAMPLE 9

3-Aminooxy-1-butylamine dihydrochloride

A mixture of 6 g (0.01794 mol) of N-[4-(N-BOC-amino)-butyl-2-oxy]-phthalimide and 60 ml of 15% hydrochloric acid is heated under reflux for 2 hours. The reaction mixture is then cooled to 5° C. and filtered, the residue on the filter is washed with water and the filtrate is concentrated to about ⅓ of the original volume. After renewed filtration, the filtrate is evaporated in vacuo and the residue is recrystallized from ethanol. The title compound is thus obtained, m.p. 160°–162° C. (decomp.).

The starting compounds are prepared as follows:

a) N-[4-(N-BOC-amino)-butyl-2-oxy]-phthalimide

A solution of 9.1 ml (0.0544 mol) of diethyl azodicaxboxylate (93%) in 50 ml of benzene is added dropwise to a mixture of 10 g (0.05284 mol) of 4-(N-BOC-amino)-butan-2-ol, 8.62 g (0.05284 mol) of N-hydroxyphthalimide, 13.86 g (0.05284 mol) of triphenylphosphine and 100 ml of benzene at 20°–30° C., while stirring. The reaction mixture is stirred at room temperature for 15 hours, in each case ¹/₁₀ of the contents by weight originally employed of N-hydroxyphthalimide, triphenylphosphine and diethyl azocticarboxylate is added again and stirring is continued for 24 hours. After filtration and evaporation of the filtrate in vacuo, the residue is purified by means of filtration on silica gel using tert-butyl methyl ether. The combined product-containing fractions are evaporated in vacuo and the residue is taken up in toluene. The mixture is cooled to 0° C. and filtered, and hexane is added to the filtrate, the title compound being obtained in crystalline form, m.p. 78°–80° C.

b) 4-(N-BOC-amino)-butan-2-ol

A solution of 78.13 g (0.358 mol) of di-tert-butyl dicarbonate in 450 ml of methylene chloride is added dropwise to a solution of 29.5 g (0.331 mol) of 4-amino-butan-2-ol [Acta Chem. Scand. 12, 1746 (1958)] in 250 ml of methylene chloride and the mixture is stirred at room temperature for 15 hours. After evaporation of the reaction mixture in vacuo, washing of the residue obtained as an oil with hexane and drying in vacuo at 50° C., the title compound is obtained as an oil, R$_f$ value=0.42 (silica gel/tert-butyl methyl ether).

EXAMPLE 10

4-Aminooxy-3-methyl-2-butylamine sulfate

A mixture of 1.45 g (0.00383 mol) of N-(2-methyl-3-phthalimido-butyl-1-oxy)-phthalimide, 0.57 ml (0.0115 mol) of hydrazine hydrate, 20 ml ethanol and 10 ml of methylenchloride is refluxed for 2 hours. It is then cooled to 0° C. and filtered, the filtrate is evaporated in vacuo and the residue is taken up in methylene chloride. After renewed filtration, the filtrate is evaporated in vacuo, 6 ml of hydrazine hydrate are added to the residue and the mixture is stirred at room temperature for a further 2 hours. The reaction mixture is then extracted thoroughly with methylene chloride and the combined methylene chloride extracts are washed with brine, dried over sodium sulfate and evaporated in vacuo. The residue is dissolved in 25 ml of ethanol, and 3.7 ml of 2N sulfuric acid are added to the solution. After evaporation in vacuo and crystallization of the residue from methanol/water, the title compound is obtained, m.p. 230°–232° C. (decomp.).

The starting compounds are prepared as follows:

a) N-(2-Methyl-3-phthalimido-butyl-1-oxy)-phthalimide 8.36 ml (0.05 mol) of diethyl azodicarboxylate (93%) are added dropwise to a solution of 10 g of crude (0.0401 mol) N-(3-hydroxy-2-methyl-butyl-1-oxy)-phthalimide, 5.9 g (0.0401 mol) of phthalimide and 13.12 g (0.05 mol) of triphenylphosphine in 75 ml of N,N-dimethylformamide at 20°–30° C., while stirring and under a nitrogen atmosphere. The reaction mixture is further stirred at room temperature for 15 hours and then evaporated in vacuo. The residue is suspended in 150 ml of toluene, the suspension is filtered and the filtrate is evaporated in vacuo. The residue is taken up in 120 ml of ether, the resulting suspension is filtered again and the filtrate is evaporated in vacuo. The residue is purified by means of flash chromatography on silica gel of particle size 0.04–0.063 mm using ethyl acetate/hexane (1:4 and 1:2). After evaporation of the product-containing fractions, the resinous title compound is obtained, R$_f$ value=0.36 (silica gel/ethyl acetate:hexane (2:3)).

b) N-(3-Hydroxy-2-methyl-butyl-1-oxy)-phthalimide 111.4 ml (0.2328 mol) of a 38% solution of diethyl azodicarboxylate in toluene are added dropwise to a mixture of 23.1 g (0.2218 mol) of 2-methyl-l,3-butanediol (Justus Liebigs Ann. Chem. 573, 227 (1951)), 36.18 g (0.2218 mol) of N-hydroxyphthalimide, 61.08 g (0.2328 mol) of triphenylphosphine and 600 ml of toluene at 10° C., while stirring and under a nitrogen atmosphere. The reaction mixture is stirred at room temperature for 15 hours and faltered and the filtrate is evaporated in vacuo. The residue is taken up in 500 ml of ether, the resulting suspension is filtered again and the filtrate is evaporated in vacuo. The residue is purified by means of flash chromatography on silica gel of particle size 0.04–0.063 mm using tert-butyl methyl ether/hexane (6:4 and 7:3). After evaporation of the product-containing fractions, the crude title compound is obtained as an oil, R$_f$ value=0.26 (silica gel/tert-butyl methyl ether:hexane (7:3)).

EXAMPLE 11

Capsules

Capsules containing 0.25 g of active ingredient, for example one of the compounds of Examples 1–9, can be prepared as follows:

Composition (for 5000 capsules)

| | |
|---|---|
| Active ingredient | 1250 g |
| Talc | 180 g |
| Wheat starch | 120 g |
| Magnesium stearate | 80 g |
| Lactose | 20 g |

The pulverulent substances are forced through a sieve of mesh width 0.6 mm and mixed. Gelatin capsules are filled with portions of in each case 0.33 g of the mixture by means of a capsule filling machine.

EXAMPLE 12

Pharmacological data

The following results were obtained for inhibition of ODC from the rat liver (see above, Seely and Pegg and Hayashi and Kameji) with determination of the $IC_{50}$ and for inhibition of the tumour growth of T24 bladder carcinoma cells (described above) with determination of the $IC_{50}$:

| Compound from Example | ODC inhibition $IC_{50}$ (µM) | T24 inhibition $IC_{50}$ (µM) |
|---|---|---|
| 1 | 0.088 | 8.1 |
| 2 | 0.027 | 5.49 |
| 3 | 0.019 | 3.76 |
| 4 | 0.36 | |
| 5 | 0.30 | |
| 6 | 0.44 | |
| 7 | 0.027 | 2.74 |
| 9 | 0.41 | |
| 10 | 0.32 | |

What is claimed is:

1. A compound of the formula I

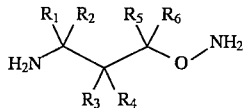

in which a) four of the radicals $R_1$, $R_2$, $R_3$, $R_4$, $R_5$ and $R_6$ are hydrogen and the others independently of one another are in each case $C_1$–$C_2$alkyl, these groups being bonded to the same carbon atom or to two different carbon atoms, or b) five of the radicals $R_1$, $R_2$, $R_3$, $R_4$, $R_5$ and $R_6$ are hydrogen and the other radical is $C_1$–$C_2$alkyl or hydroxymethyl, or a salt thereof.

2. A compound of the formula I according to claim 1, in which a) four of the radicals $R_1$, $R_2$, $R_3$, $R_4$, $R_5$ and $R_6$ are hydrogen and the others independently of one another are in each case $C_1$–$C_2$alkyl, these groups being bonded to the same or to two different carbon atoms, or b) five of the radicals $R_1$, $R_2$, $R_3$, $R_4$, $R_5$ and $R_6$ are hydrogen and the other radical is $C_1$–$C_2$alkyl, or a salt thereof.

3. A compound of the formula I according to claim 1, in which a) four of the radicals $R_1$, $R_2$, $R_3$, $R_4$, $R_5$ and $R_6$ are hydrogen and the others independently of one another are in each case methyl, these groups being bonded to the same or to two different carbon atoms, or b) five of the radicals $R_1$, $R_2$, $R_3$, $R_4$, $R_5$ and $R_6$ are hydrogen and the other radical is methyl, or a salt thereof.

4. A compound of the formula I according to claim 1, in which a) four of the radicals $R_1$, $R_2$, $R_3$, $R_4$, $R_5$ and $R_6$ are hydrogen and the others independently of one another are in each case methyl, these groups being bonded to the same carbon atom, or b) five of the radicals $R_1$, $R_2$, $R_3$, $R_4$, $R_5$ and $R_6$ are hydrogen and the others independently of one another are in each case methyl, these groups being bonded to the same carbon atom, or or a salt thereof; this compound, if it contains an asymmetric carbon atom, existing as a pure enantiomer, or a salt thereof.

5. A compound of the formula I according to claim 1, in which one of the radicals $R_1$ and $R_2$ is $C_1$–$C_2$alkyl and the other is hydrogen and each of the radicals $R_3$, $R_4$, $R_5$ and $R_6$ is hydrogen;

or a salt thereof.

6. A compound of the formula I according to claim 1, in which one of the radicals $R_1$ and $R_2$ is methyl and the other is hydrogen and each of the radicals $R_3$, $R_4$, $R_5$ and $R_6$ is hydrogen;

or a salt thereof.

7. A compound of the formula I according to claim 1, in which one of the radicals $R_1$ and $R_2$ is $C_1$–$C_2$alkyl and the other is hydrogen and each of the radicals $R_3$, $R_4$, $R_5$ and $R_6$ is hydrogen;

which exists as a pure enantiomer, or a salt thereof.

8. A compound of the formula I according to claim 1, in which one of the radicals $R_1$ and $R_2$ is methyl and the other is hydrogen and each of the radicals $R_3$, $R_4$, $R_5$ and $R_6$ is hydrogen;

which exists as a pure enantiomer, or a salt thereof.

9. A compound of the formula I according to claim 1, in which one of the radicals $R_3$ and $R_4$ is $C_1$–$C_2$alkyl and the other is hydrogen and each of the radicals $R_1$, $R_2$, $R_5$ and $R_6$ is hydrogen;

or a salt thereof.

10. A compound of the formula I according to claim 1, in which one of the radicals $R_3$ and $R_4$ is methyl and the other is hydrogen and each of the radicals $R_1$, $R_2$, $R_5$ and $R_6$ is hydrogen;

or a salt thereof.

11. A compound of the formula I according to claim 1, in which one of the radicals $R_3$ and $R_4$ is $C_1$–$C_2$alkyl and the other is hydrogen and each of the radicals $R_1$, $R_2$, $R_5$ and $R_6$ is hydrogen;

which exists as a pure enantiomer, or a salt thereof.

12. A compound of the formula I according to claim 1, in which one of the radicals $R_3$ and $R_4$ is methyl and the other is hydrogen and each of the radicals $R_1$, $R_2$, $R_5$ and $R_6$ is hydrogen;

which exists as a pure enantiomer, or a salt thereof.

13. A compound of the formula I according to claim 1, in which one of the radicals $R_5$ and $R_6$ is $C_1$–$C_2$alkyl and the other is hydrogen and each of the radicals $R_1$, $R_2$, $R_3$ and $R_4$ is hydrogen;

or a salt thereof.

14. A compound of the formula I according to claim 1, in which one of the radicals $R_5$ and $R_6$ is methyl and the other is hydrogen and each of the radicals $R_1$, $R_2$, $R_3$ and $R_4$ is hydrogen;

or a salt thereof.

15. A compound of the formula I according to claim 1, in which one of the radicals $R_5$ and $R_6$ is $C_1$–$C_2$alkayl and the other is hydrogen and each of the radicals $R_1$, $R_2$, $R_3$ and $R_4$ is hydrogen;

which exists as a pure enantiomer, or a salt thereof.

16. A compound of the formula I according to claim 1, in which one of the radicals $R_5$ and $R_6$ is methyl and the other is hydrogen and each of the radicals $R_1$, $R_2$, $R_3$ and $R_4$ is hydrogen;

which exists as a pure enantiomer, or a salt thereof.

17. A compound of the formula I according to claim 1, in which one of the radicals $R_1$, $R_2$, $R_3$, $R_4$, $R_5$ and $R_6$ is hydroxymethyl, while each of the other radicals is hydrogen;

or a salt thereof.

18. A compound of the formula I according to claim 1, in which one of the radicals $R_1$, $R_2$, $R_3$, $R_4$, $R_5$ and $R_6$ is hydroxymethyl, while each of the other radicals is hydrogen;

the corresponding compound of the formula I existing as a pure enantiomer, or a salt thereof.

19. A compound of the formula I according to claim 1, in which each of the radicals $R_1$ and $R_2$ is selected from the group consisting of hydrogen, $C_1$–$C_2$alkyl and hydroxymethyl, with the provisos that if one of these two radicals is hydroxymethyl the other is hydrogen, and that not more than one of the radical $R_1$ and $R_2$ is hydrogen;

and in which $R_3$, $R_4$, $R_5$ and $R_6$ are hydrogen;

or a salt thereof.

20. A compound of the formula I according to claim 1, in which each of the radicals $R_1$ and $R_2$ is chosen from the group consisting of hydrogen, $C_1$–$C_2$alkyl and hydroxymethyl, with the provisos that if one of these two radicals is hydroxymethyl the other is hydrogen, and that not more than one of the radicals $R_1$ and $R_2$ is hydrogen;

and in which $R_3$, $R_4$, $R_5$ and $R_6$ are hydrogen;

this compound existing as a pure enantiomer, if the radicals $R_1$ and $R_2$ differ from one another, or a salt thereof.

21. A compound of the formula I according to claim 1, in which each of the radicals $R_1$ and $R_2$ is chosen from the group consisting of hydrogen and $C_1$–$C_2$alkyl, with the provisos that not more than one of the radicals $R_1$ and $R_2$ is hydrogen;

and in which $R_3$, $R_4$, $R_5$ and $R_6$ are hydrogen;

this compound existing as a pure (S) enantiomer, if the radicals $R_1$ and $R_2$ differ from one another, or a salt thereof.

22. A compound of the formula I according to claim 1, in which one of the radicals $R_1$, $R_2$, $R_3$, $R_4$, $R_5$ and $R_6$ is $C_1$–$C_2$alkyl;

or a salt thereof.

23. A compound of the formula I according to claim 1, in which one of the radicals $R_1$, $R_2$, $R_3$, $R_4$, $R_5$ and $R_6$ is methyl;

or a salt thereof.

24. A compound of the formula I according to claim 1, in which one of the radicals $R_1$, $R_2$, $R_3$, $R_4$, $R_5$ and $R_6$ is methyl;

this compound existing as a pure enantiomer; or a salt thereof.

25. A compound of the formula I according to claim 1, in which one of the radicals $R_1$, $R_2$, $R_3$, $R_4$, $R_5$ and $R_6$ is $C_1$–$C_2$alkyl;

this compound existing in an (S) configuration, or a salt thereof.

26. A compound of the formula 1 according to claim 1, in which one of the radicals $R_1$, $R_2$, $R_3$, $R_4$, $R_5$ and $R_6$ is methyl;

this compound existing in an (S) configuration, or a salt thereof.

27. A compound of the formula I according to claim 1, in which one of the radicals $R_1$, $R_2$, $R_3$, $R_4$, $R_5$ and $R_6$ is $C_1$–$C_2$alkyl;

this compound existing in an (R) configuration, or a salt thereof.

28. A compound of the formula I according to claim 1, in which one of the radicals $R_1$, $R_2$, $R_3$, $R_4$, $R_5$ and $R_6$ is methyl;

this compound existing in an (R) configuration, or a salt thereof.

29. (2S)-4- Aminooxy-2-butylamine according to claim 1, or a pharmaceutically acceptable salt thereof.

30. (2R)-4-Aminooxy-2-butylamine according to claim 1, or a pharmaceutically acceptable salt thereof.

31. 4-Aminooxy-2-butylamine according to claim 1, or a pharmaceutically acceptable salt thereof.

32. 5-Aminooxy-3-pentylamine according to claim 1, or a pharmaceutically acceptable salt thereof.

33. 4-Aminooxy-2-methyl-2-butylamine according to claim 1, or a pharmaceutically acceptable salt thereof.

34. (2S)-4-Aminooxy-1-hydroxy-2-butylamine according to claim 1, or a pharmaceutically acceptable salt thereof.

35. 3-Aminooxy-2-methyl-1-propylamine according to claim 1, or a pharmaceutically acceptable salt thereof.

36. 4-Aminooxy-3-methyl-2-butylamine according to claim 1, or a pharmaceutically acceptable salt thereof.

37. A pharmaceutical composition for the treatment or prophylaxis of a disease in warm-blooded animals which responds to inhibition of ornithine decarboxylase and comprises an amount of a compound of the formula I according to claim 1, or of a pharmaceutically acceptable salt thereof according to claim 1, which is active against diseases which respond to inhibition of ornithine decarboxylase, together with a pharmaceutically acceptable carrier.

38. A method for the treatment of a benign or malignant tumour disease which responds to inhibition of ornithine decarboxylase, which comprises administration of a prophylactically or therapeutically active, ornithine decarboxylase-inhibiting amount of a compound of the formula I or of a pharmaceutically acceptable salt thereof according to claim 1, to a warm-blooded animal requiring such treatment.

39. A process for the preparation of a compound of the formula I according to claim 1, which comprises a procedure in which from a compound of the formula II

$$X_1X_2N\text{---}(CR_1R_2)\text{---}(CR_3R_4)\text{---}(CR_5R_6)\text{-O-}NX_3X_4 \qquad (II)$$

in which the radicals $R_1$, $R_2$, $R_3$, $R_4$, $R_5$ and $R_6$ are as defined for compounds of the formula I and in which $X_1$, $X_2$, $X_3$ and $X_4$ independently of one another are hydrogen or a monovalent amino-protecting group, and in which $X_1$ with $X_2$, $X_3$ with $X_4$ or $X_1$ with $X_2$ and $X_3$ with $X_4$ can also in each case together be a bivalent protecting group, and in which other functional groups which are not to participate in the reaction are present in protected form if necessary, with the proviso that at least one of the groups $X_1$, $X_2$, $X_3$ and $X_4$ is an amino-protecting group, or a salt thereof if salt-forming groups present, amino-protecting groups present are split off, and, if desired a compound of the formula I which is obtainable is converted into another compound of the formula I, an isomer mixture which is obtainable is split into the isomers and/or a free compound of the formula I which is obtainable is converted into a salt or a salt of a compound of the formula I which is obtainable is converted into the free compound or into another salt.

* * * * *